(12) United States Patent
Meng et al.

(10) Patent No.: US 8,592,396 B2
(45) Date of Patent: Nov. 26, 2013

(54) GLUCOKINASE ACTIVATORS AND METHODS OF USING SAME

(75) Inventors: Wei Meng, Pennington, NJ (US); Peter T. W. Cheng, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/640,767

(22) PCT Filed: Apr. 14, 2011

(86) PCT No.: PCT/US2011/032386
§ 371 (c)(1),
(2), (4) Date: Oct. 12, 2012

(87) PCT Pub. No.: WO2011/130459
PCT Pub. Date: Oct. 20, 2011

(65) Prior Publication Data
US 2013/0029939 A1    Jan. 31, 2013

Related U.S. Application Data

(60) Provisional application No. 61/323,957, filed on Apr. 14, 2010.

(51) Int. Cl.
*A01N 57/00* (2006.01)
*A61K 31/675* (2006.01)

(52) U.S. Cl.
USPC .......................................... 514/80; 514/244

(58) Field of Classification Search
None
See application file for complete search history.

(56) References Cited

U.S. PATENT DOCUMENTS

| | | |
|---|---|---|
| 7,407,946 B2 | 8/2008 | Mortlock |
| 7,514,460 B2 | 4/2009 | Herz et al. |
| 7,687,502 B2 | 3/2010 | Mitsuya et al. |
| 7,863,283 B2 | 1/2011 | Nguyen et al. |
| 7,910,747 B2 * | 3/2011 | Ryono et al. ............... 548/375.1 |
| 8,232,284 B2 | 7/2012 | Iino et al. |
| 2006/0046987 A1 | 3/2006 | Mortlock et al. |
| 2007/0149523 A1 | 6/2007 | Ehlert et al. |

* cited by examiner

*Primary Examiner* — Brandon Fetterolf
*Assistant Examiner* — Jean Cornet
(74) *Attorney, Agent, or Firm* — Burton Rodney

(57) ABSTRACT

Compounds are provided which are activators of the enzyme glucokinase and thus are useful in treating diabetes and related diseases, which compounds have the structure wherein $R_1$, $R_2$, $R_3$, $R_4$, $R_5$, $R_6$, Y and X are as defined herein or a pharmaceutically acceptable salt thereof. A method for treating diabetes and related disease employing the above compounds is also provided.

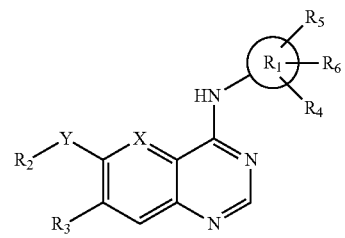

(I)

12 Claims, No Drawings

GLUCOKINASE ACTIVATORS AND METHODS OF USING SAME

CROSS-REFERENCE TO RELATED APPLICATIONS

This application claims the benefit of U.S. Provisional Application Ser. No. 61/323,957 filed Apr. 14, 2010.

FIELD OF THE INVENTION

The present invention relates to novel phosphonate and phosphinate compounds which are activators of the enzyme glucokinase and thus are useful in treating diabetes, and to a method for treating diabetes, especially Type II diabetes, using such compounds.

BACKGROUND OF THE INVENTION

The enzyme glucokinase (GK), which is mainly found in pancreatic β-cells and liver parenchymal cells, catalyzes the conversion of glucose to glucose-6-phosphate, which is the first step in the metabolism of glucose. Glucokinase is also a rate-controlling enzyme for glucose metabolism in pancreatic β-cells and liver parenchymal cells, which play an important role in whole-body glucose homeostasis.

Liag, Y. et al. (*Biochem. J.*, 309:167-173 (1995)) report the finding that Type II (maturity-onset) diabetes of the young (MODY-2) is caused by loss of function mutations in the glucokinase gene, which suggests that glucokinase also functions as a glucose sensor in humans. Thus, compounds that activate glucokinase and thus increase the sensitivity of the glucokinase sensor system and thereby cause increase in insulin secretion will be useful in the treatment of hyperglycemia and Type II diabetes.

Glucokinase activators have been demonstrated to be effective in enhancing: 1) the effect of glucose on insulin release from isolated rat and human pancreatic islets, and 2) the glucose induction of pancreatic islet glucokinase in isolated cultured rat islets (e.g., Matschinsky, F. M. et al., *Diabetes*, 55:1 (2006), and (Matschinsky, F. M. et al., eds., *Glucokinase and Glycemic Disease, from Basics to Novel Therapeutics*, Karger, publ., Ch. 6, pp. 360-378 (2004)). In diabetic animal model studies, glucokinase activators have been demonstrated to stimulate insulin release, enhance glycogen synthesis and reduce hepatic glucose production in pancreatic clamp studies. Importantly, glucokinase activators have been demonstrated to dose-dependently lower blood glucose levels in different standard animal models of type 2 diabetes, such as the ob/ob mouse, db/db mouse and Zucker fa/fa rat in acute single-dose studies and also effectively improved the glucose excursion in both normal C57/BL6J and ob/ob mice in oral glucose tolerance tests (e.g., in Matschinsky, F. M. et al., eds., *Glucokinase and Glycemic Disease, from Basics to Novel Therapeutics*, Karger, publ., Ch. 6, pp. 360-378 (2004); as well as Fyfe, M. C. et al., *Diabetologia*, 50:1277 (2007)).

Glucokinase activators have also demonstrated antidiabetic efficacy in chronic animal models of type II diabetes. For instance, in a 9-day study in ob/ob mice, a glucokinase activator improved the overall glucose profile while showing comparable antihyperglycemic effects in oral glucose tolerance tests at the beginning and end of the study (Fyfe, M. C. et al., *Diabetologia*, 50:1277 (2007)). In another instance, in a chronic 40-week study, a glucokinase activator prevented the development of hyperglycemia in diet-induced obese mice which were glucose intolerant. The diet-induced obese mice treated with a glucokinase activator showed marked improvement in the glucose excursion in an oral glucose tolerance test at the end of the study relative to the control group Matschinsky, F. M. et al., eds., *Glucokinase and Glycemic Disease, from Basics to Novel Therapeutics*, Karger, publ., Ch. 6, pp. 360-378 (2004)).

SUMMARY OF THE INVENTION

In accordance with one aspect of the invention, compounds are provided having the structure I

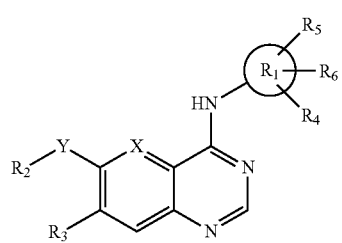

wherein $R_1$ is a 5- or 6-membered monocyclic heteroaryl substituted by $R_4$, and optionally substituted with one or two substituents $R_5$ and/or $R_6$, wherein the heteroaryl possesses a nitrogen atom adjacent to —NH—;

$R_4$ is —(CH$_2$)$_n$—Z—(CH$_2$)$_m$—PO(OR$_7$)(OR$_8$),
or —(CH$_2$)$_n$Z—(CH$_2$)$_m$—PO(OR$_7$)R$_9$,
or —(CH$_2$)$_n$—Z—(CH$_2$)$_m$—O—PO(OR$_7$)R$_9$,
or —(CH$_2$)$_n$Z—(CH$_2$)$_m$—O—PO—(R$_9$)R$_{10}$,
or —(CH$_2$)$_n$Z—(CH$_2$)$_m$—PO(R$_9$)R$_{10}$, where $R_4$ is connected to $R_1$ through a ring nitrogen or carbon;

$R_7$ and $R_8$ are the same or different and are independently selected from $C_1$-$C_3$ alkyl;

$R_9$ and $R_{10}$ are the same or different and are independently selected from $C_1$-$C_3$ alkyl, phenyl, phenyl-$C_1$-$C_3$-alkyl, 5- to 6-membered heteroaryl and 5- to 6-membered heteroaryl-$C_1$-$C_3$-alkyl, any of which may be optionally substituted;

additionally, $R_7$ and $R_8$ can be cyclized into a ring

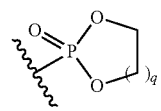

where q=1 to 3;

similarly, $R_7$ and $R_9$ can be cyclized into a ring

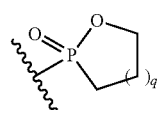

where q=1 to 3, or

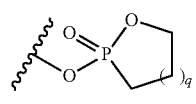

where q=1 to 3;

similarly, $R_9$ and $R_{10}$ can be cyclized into a ring

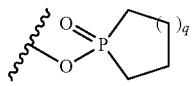

where q=1 to 3, or

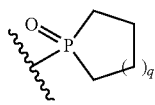

where q=1 to 3;

Z is selected from a bond, $C_1$-$C_3$ alkylene and $C_2$-$C_4$ alkenylene, each of which may be optionally substituted (e.g., hydroxy, $C_1$-$C_3$ alkoxy, amino-$C_1$-$C_3$-alkyl, aminophenyl-$C_1$-$C_3$-alkyl, 5- to 6-membered heteroaryl-$C_1$-$C_3$-alkyl, amino 5- to 6-membered heteroaryl-$C_1$-$C_3$-alkyl, 5- to 6-membered heteroaryl-$C_1$-$C_3$-alkyl, aminophenyl, amino 5- to 6-membered heteroaryl or carboxy);

m is 0, 1 or 2;

n is 0, 1 or 2;

and Z may be O, S, $SO_2$ when m is 1 or 2 or n is 1 or 2;

$R_5$ and $R_6$ are the same or different and are independently selected from hydrogen, $C_1$-$C_3$ alkyl, halogen or carboxyl, or is absent;

X is N or CH;

Y is O or S;

$R_3$ is H, halogen, $C_1$-$C_3$ alkyl, OH, OMe, SH, or SMe;

$R_2$ is $C_1$-$C_6$ alkyl or branched $C_3$-$C_6$ alkyl, $C_3$-$C_6$ cycloalkyl, $C_3$-$C_6$ cycloalkyl-$C_1$-$C_3$-alkyl, phenyl, phenyl-$C_1$-$C_3$-alkyl, 5- to 6-membered heteroaryl, or 5- to 6-membered heteroaryl-$C_1$-$C_3$-alkyl;

wherein each $R_2$ is independently optionally substituted by one to three $R_1$ groups;

each $R_{11}$ is independently selected from halogen, —$CH_{3-a}F_a$, CN, $NO_2$, $NH_2$, $C_1$-$C_3$ alkyl, O—$C_1$-$C_3$-alkyl, —COOH, OH, phenyloxy, 5- to 6-membered heteroaryloxy, 4- to 7-membered heterocyclyloxy, —S—$R_{12}$, —S(O)—$R_{12}$, —$SO_2R_{13}$, —$SO_2NR_{14}R_{15}$, —$NR_{14}R_{15}$, —$CO_2R_{13}$, —C(O)$NR_{14}R_{15}$, N-linked amide (—$NR_7C(O)R_{15}$), N-linked sulfonamide (—$NR_7SO_2R_{12}$), N— linked carbamate (—$NR_7CO_2R_{12}$), O— linked carbamate (—$OCONR_{14}R_{15}$), N-linked urea (—$NR_7C(O)NR_{14}R_{15}$), phenyl, 5- to 6-membered heteroaryl, or 4- to 7-membered heterocyclyl;

wherein each phenyl, heteroaryl, or heterocyclyl ring in $R_{11}$ is optionally substituted by halogen, —$CH_{3-a}F_a$, CN, $NO_2$, $NH_2$, —COOH, OH, $C_1$-$C_3$ alkyl, —O—$C_1$-$C_3$-alkyl, —C(O)O—$C_1$-$C_3$-alkyl, —$NR_{14}R_{15}$, —C(O)$NR_{14}R_{15}$, N-linked amide (—$NR_7COR_{15}$), N-linked sulfonamide (—$NR_7SO_2R_{12}$), N-linked carbamate (—$NR_7COOR_{12}$), N— linked urea (—$NR_7CONR_{14}R_{15}$), sulfonamide (—$SO_2NR_{14}R_{15}$);

each "a" is independently an integer selected from 1, 2 or 3;

each $R_{12}$ is independently selected from $C_1$-$C_3$ alkyl, phenyl, 5- to 6-membered heteroaryl, phenyl-$C_1$-$C_3$-alkyl, or 5- to 6-membered heteroaryl-$C_1$-$C_3$-alkyl;

each $R_{13}$ is independently selected from H, $C_1$-$C_3$ alkyl, phenyl, 5- to 6-membered heteroaryl, phenyl-$C_1$-$C_3$-alkyl, or 5- to 6-membered heteroaryl-$C_1$-$C_3$-alkyl;

$R_{14}$ and $R_{15}$ are the same or different and are independently selected from H, $C_1$-$C_3$ alkyl, $C_3$-$C_6$ cycloalkyl, phenyl, phenyl-$C_1$-$C_3$-alkyl, 5- to 6-membered heteroaryl or 5- to 6-membered heteroaryl-$C_1$-$C_3$-alkyl or $R_{14}$ and $R_{15}$ cyclized together to form a 3- to 7-membered heterocyclyl; and all stereoisomers thereof, a prodrug ester thereof, or a pharmaceutically acceptable salt thereof.

Preferably in compounds of formula I

X is CH;

the moiety is preferably

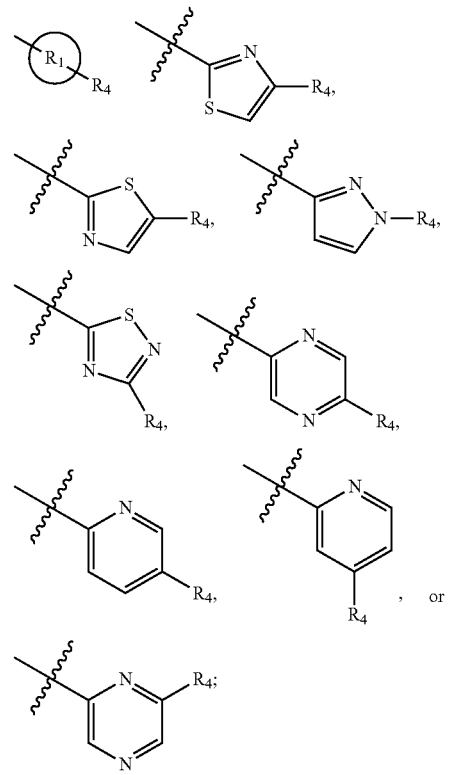

$R_4$ is preferably —$(CH_2)_n$—Z—$(CH_2)_m$—$PO(OR_7)(OR_8)$ where Z is preferably a bond and n is preferably 1 or 2; or —$(CH_2)_n$—Z—$(CH_2)_m$—$PO(OR_7)R_9$ where Z is preferably a bond and n is preferably 1 or 2;

$R_4$ is more preferably

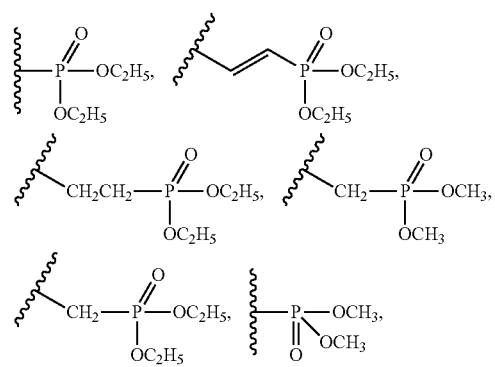

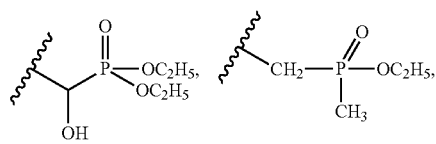

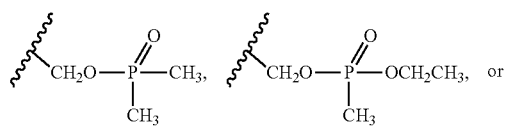

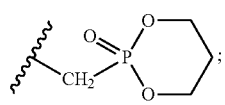

Y is preferably —O—;

R$_3$ is preferably hydrogen;

R$_2$ is preferably C$_1$-C$_3$ alkyl, halo-C$_1$-C$_3$-alkyl, dihalo-C$_1$-C$_3$-alkyl, C$_1$-C$_3$-alkoxy-C$_1$-C$_3$-alkyl, or 4- to 7-membered heterocyclo, more preferably

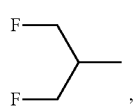

i-propyl,

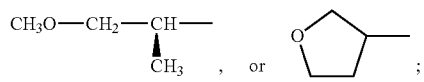

R$_5$ and R$_6$ are each preferably hydrogen; and

Z is preferably a bond or CH$_2$.

Examples of preferred compounds in accordance with the present invention include, but are not limited to, the following:

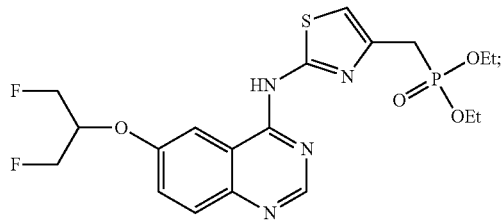

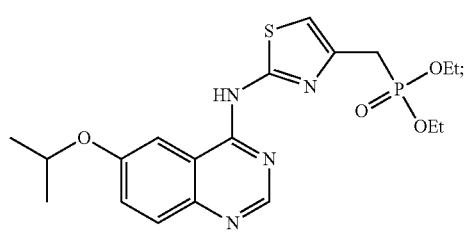

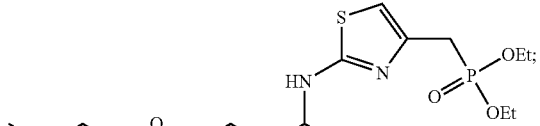

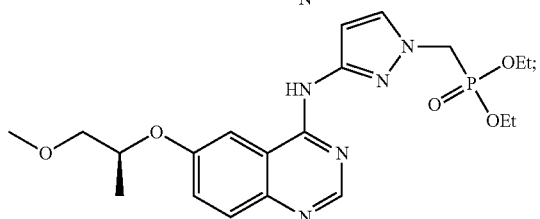

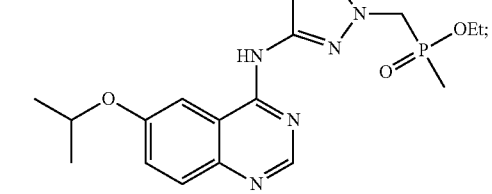

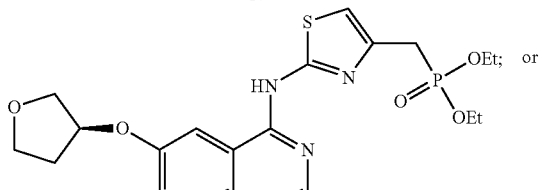

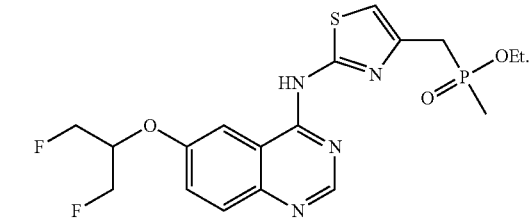

The compounds of the present invention activate or enhance the activity of the enzyme glucokinase. Consequently, the compounds of the present invention may be used in the treatment of multiple diseases or disorders associated with a deficit of glucokinase, such as diabetes and related conditions, microvascular complications associated with diabetes, the macrovascular complications associated with diabetes, cardiovascular diseases, Metabolic Syndrome and its component conditions, and other maladies. Examples of diseases or disorders associated with deficit in activity of the enzyme glucokinase that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

The present invention provides for compounds of formula I, pharmaceutical compositions employing such compounds, and for methods of using such compounds. In particular, the present invention provides a pharmaceutical composition containing a therapeutically effective amount of a compound of formula I, alone or in combination with a pharmaceutically acceptable carrier.

Further, in accordance with the present invention, a method is provided for preventing, inhibiting, or treating the progression or onset of diseases or disorders associated with deficit in the activity of the enzyme glucokinase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other therapeutic agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

In another embodiment, compounds of the present invention are selected from the compounds exemplified in the examples.

In another embodiment, the present invention relates to pharmaceutical compositions which include of a therapeutically effective amount of a compound of the present invention, alone or, optionally, in combination with a pharmaceutically acceptable carrier and/or one or more other agent(s).

In another embodiment, the present invention relates to methods of enhancing the activity of the enzyme glucokinase which includes the step of administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with deficit in the activity of the enzyme glucokinase which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the deficit in activity of the enzyme glucokinase that can be prevented, inhibited, or treated according to the present invention include, but are not limited to, are those diseases or disorders set out above.

In another embodiment, the present invention relates to a method for preventing, inhibiting, or treating the progression or onset of diabetes, hyperglycemia, obesity, dyslipidemia, hypertension, and cognitive impairment which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dyslipidemia, which includes the step of administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Another embodiment of the invention relates to the use of a compound of formula I in the manufacture of a medicament for the treatment of diabetes.

Another embodiment of the invention relates to the compound of formula I of the invention for use in therapy in treating diabetes.

Another embodiment of the invention relates to the compound of formula I of the invention for use in treating diabetes in a mammal.

Another embodiment of the invention relates to the use of a compound of formula I of the invention in the manufacture of a medicament for treatment of diabetes, in which such treatment comprises a combination with another therapeutic agent, for concurrent or sequential use, in any order.

Another embodiment of the invention relates to the combination of a compound of formula I of the invention and another therapeutic agent as a medicament for the treatment of diabetes.

DETAILED DESCRIPTION OF THE INVENTION

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms, and all geometric isomeric forms of a structure are intended, unless the specific stereochemistry or isomeric form is specifically indicated.

The term "substituted," as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "lower alkyl," "alkyl," or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1-C_4$ alkylene)$NR_aR_b$, —$C(=O)NR_a(SO_2)R_b$, —$CO_2(C_1-C_4$ alkylene)$NR_aR_b$, —$NR_aC(=O)R_b$, —$NR_aCO_2R_b$, —$NR_a(C_1-C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$ (alkyl), $C_3-C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_1-C_6)$alkyl, $(C_2-C_6)$alkenyl, hydroxy, halogen, cyano, nitro, $CF_3$, $O(C_1-C_6$ alkyl), $OCF_3$, $C(=O)H$, $C(=O)(C_1-C_6$ alkyl), $CO_2H$, $CO_2(C_1-C_6$ alkyl), $NHCO_2(C_1-C_6$ alkyl), —$S(C_1-C_6$ alkyl), —$NH_2$, $NH(C_1-C_6$ alkyl), $N(C_1-C_6$ alkyl)$_2$, $N(CH_3)_3^+$, $SO_2(C_1-C_6$ alkyl), $C(=O)(C_1-C_4$ alkylene)$NH_2$, $C(=O)(C_1-C_4$ alkylene)NH(alkyl), $C(=O)(C_1-C_4$ alkylene)$N(C_1-C_4$ alkyl)$_2$, $C_3-C_7$cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

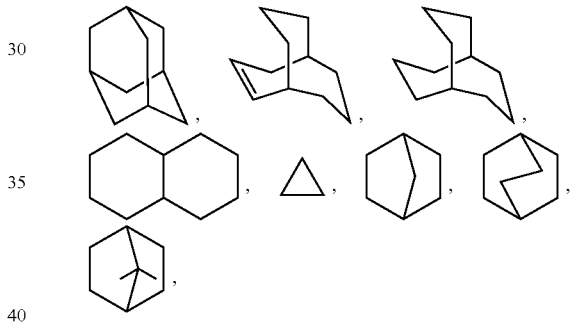

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

Unless otherwise indicated, the term "aryl" as employed herein alone or as part of another group refers to monocyclic and bicyclic aromatic groups containing 6 to 10 carbons in the ring portion (such as phenyl, biphenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings)

for example

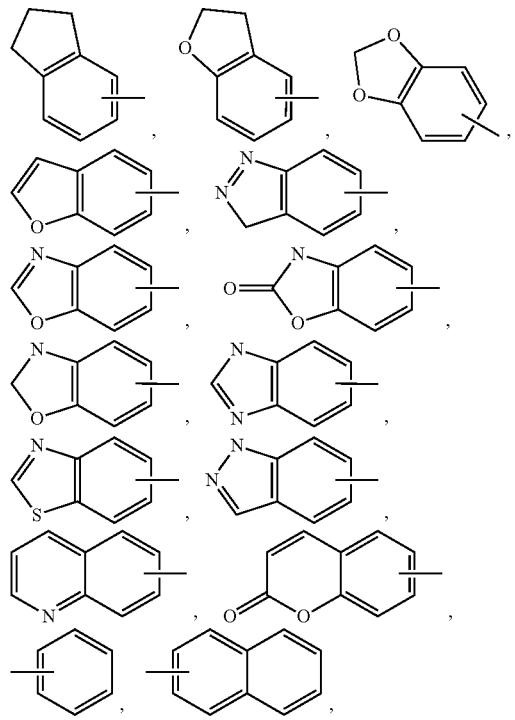

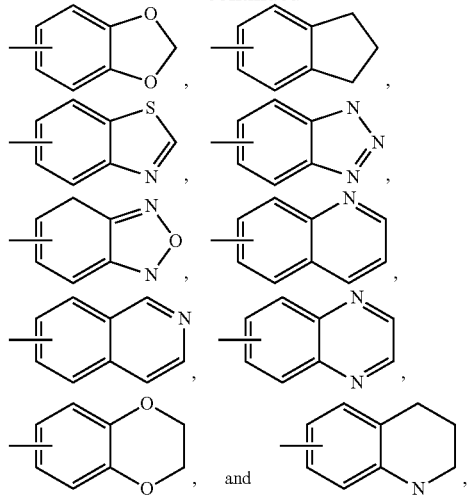

as well as such groups including 2 free bonds and thus are linking groups.

The aryl group may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1$-$C_4$ alkylene)$NR_aR_b$, —$C(=O)NR_a(SO_2)R_b$, —$CO_2(C_1$-$C_4$ alkylene)$NR_aR_b$, —$NR_aC(=O)R_b$, —$NR_aCO_2R_b$, or —$NR_a(C_1$-$C_4$ alkylene)$CO_2R_b$, wherein $R_a$, $R_b$ and $R_c$, are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_1$-$C_4)$alkyl, $(C_2$-$C_4)$alkenyl, halogen, hydroxy, cyano, nitro, $CF_3$, $O(C_1$-$C_4$ alkyl), $OCF_3$, $C(=O)H$, $C(=O)(C_1$-$C_4$ alkyl), $CO_2H$, $CO_2(C_1$-$C_4$ alkyl), $NHCO_2(C_1$-$C_4$ alkyl), —$S(C_1$-$C_4$ alkyl), —$NH_2$, $NH(C_1$-$C_4$ alkyl), $N(C_1$-$C_4$ alkyl)$_2$, $N(C_1$-$C_4$ alkyl)$_3^+$, $SO_2(C_1$-$C_4$ alkyl), $C(=O)(C_1$-$C_4$ alkylene)$NH_2$, $C(=O)(C_1$-$C_4$ alkylene)$NH(alkyl)$, and/or $C(=O)(C_1$-$C_4$ alkylene)$N(C_1$-$C_4$ alkyl)$_2$ and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R_3$ groups or substituents for $R_3$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

The term "acyl" alone or as part of another group refers to a carbonyl group linked to an organic radical, more particularly, the group $C(=O)R_e$, as well as the bivalent groups $—C(=O)—$ or $—C(=O)R_e—$, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The term "heterocyclo" or "heterocyclic" or "heterocyclyl" or "cycloheteroalkyl" refers to substituted and unsubstituted non-aromatic 3- to 7-membered monocyclic groups, 7 to 11 membered bicyclic groups, and 10- to 15-membered tricyclic groups, in which at least one of the rings has at least one heteroatom (O, S, or N) (also referred to as cycloheteroalkyl or heterocycloalkyl), as well as such groups including 2 free bonds and thus are linking groups. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), $—NR_aR_b$, $—N(alkyl)_3^+$, $—NR_aSO_2$, $—NR_aSO_2R_c$, $—SO_2R_c$— $SO_2NR_aR_b$, $—SO_2NR_aC(=O)$ $R_b$, $SO_3H$, $—PO(OH)_2$, $—C(=O)R_a$, $—CO_2R_a$, $—C(=O)$ $NR_aR_b$, $—C(=O)(C_1$-$C_4$ alkylene)$NR_aR_b$, $—C(=O)NR_a$ $(SO_2)R_b$, $—CO_2(C_1$-$C_4$ alkylene)$NR_aR_b$, $—NR_aC(=O)R_b$, $—NR_aCO_2R_b$, $—NR_a(C_1$-$C_4$ alkylene)$CO_2R_b$, $=N—OH$, $=N—O$-alkyl, aryl, cycloalkyl, heterocyclo, and/or heteroaryl, wherein $R_a$, $R_b$, and $R_c$, are as defined above for substituted alkyl groups, and are also in turn optionally substituted as recited above. When a heterocyclo is substituted with a further ring, said ring in turn is optionally substituted with one to two of $(C_1$-$C_4)$alkyl, $(C_2$-$C_4)$alkenyl, halogen, hydroxy, cyano, nitro, $CF_3$, $O(C_1$-$C_4$ alkyl), $OCF_3$, $C(=O)H$, $C(=O)(C_1$-$C_4$ alkyl), $CO_2H$, $CO_2(C_1$-$C_4$ alkyl), $NHCO_2(C_1$-$C_4$ alkyl), $—S(C_1$-$C_4$ alkyl), $—NH_2$, $NH(C_1$-$C_4$ alkyl), $N(C_1$-$C_4$ alkyl)$_2$, $N(C_1$-$C_4$ alkyl)$_3^+$, $SO_2(C_1$-$C_4$ alkyl), $C(=O)(C_1$-$C_4$ alkylene)$NH_2$, $C(=O)(C_1$-$C_4$ alkylene)NH(alkyl), and/or $C(=O)(C_1$-$C_4$ alkylene)N$(C_1$-$C_4$ alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like. Exemplary bicyclic heterocyclo groups include quinuclidinyl.

Preferred heterocyclo groups in compounds of formula (I) include

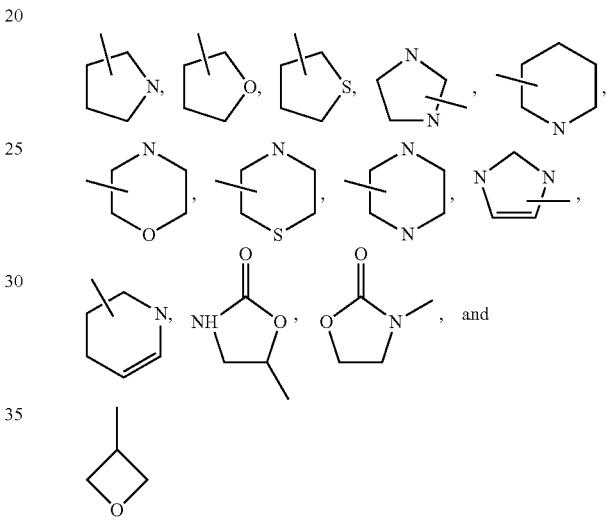

which optionally may be substituted.

The term "heteroaryl" alone or as part of another group refers to substituted and unsubstituted aromatic 5 or 6 monocyclic groups, 9- or 10-membered bicyclic groups, and 11- to 14-membered tricyclic groups which have at least one heteroatom (O, S or N) in at least one of the rings, as well as such groups including 2 free bonds and thus are linking groups. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated, and may include aryl, cycloalkyl, heteroaryl or cycloheteroaryl. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents which may be any of the substituents set out for alkyl and can be selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), $—NR_aR_b$, $—N(alkyl)_3^+$, $—NR_aSO_2$, —NR$_a$SO$_2$R$_c$, —SO$_2$R—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_1$-C$_4$ alkylene)NR$_a$R$_b$, —C(=O)NR$_a$(SO$_2$)R$_b$, —CO$_2$(C$_1$-C$_4$ alkylene)NR$_a$R$_b$, —NR$_a$C(=O)R$_b$, —NR$_a$CO$_2$R$_b$, —NR$_a$(C$_1$-C$_4$ alkylene)CO$_2$R$_b$, aryl, cycloalkyl, heterocyclo, and/or heteroaryl, wherein R$_a$, R$_b$ and R$_c$, are as defined above for substituted alkyl groups, and are also in turn optionally substituted as recited above. When a heteroaryl is substituted with a further ring, said ring in turn is optionally substituted with one to two of (C$_1$-C$_4$)alkyl, (C$_2$-C$_4$)alkenyl, halogen, hydroxy, cyano, nitro, CF$_3$, O(C$_1$-C$_4$ alkyl), OCF$_3$, C(=O)H, C(=O)(C$_1$-C$_4$ alkyl), CO$_2$H, CO$_2$(C$_1$-C$_4$ alkyl), NHCO$_2$(C$_1$-C$_4$ alkyl), —S(C$_1$-C$_4$ alkyl), —NH$_2$, NH(C$_1$-C$_4$ alkyl), N(C$_1$-C$_4$ alkyl)$_2$, N(C$_1$-C$_4$ alkyl)$_3^+$, SO$_2$(C$_1$-C$_4$ alkyl), C(=O)(C$_1$-C$_4$ alkylene)NH$_2$, C(=O)(C$_1$-C$_4$ alkylene)NH(alkyl), and/or C(=O)(C$_1$-C$_4$ alkylene)N(C$_1$-C$_4$ alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

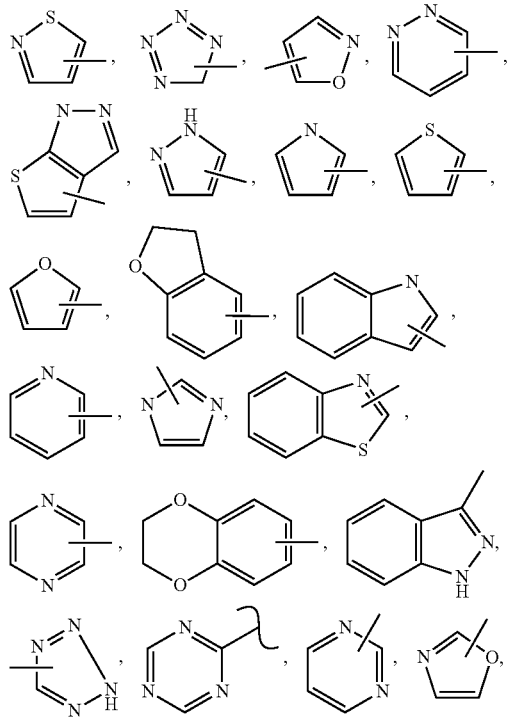

-continued

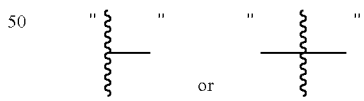

and the like.

The term "heterocyclylalkyl" or "heterocycloalkyl" or "cycloheteroalkylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an —OH group.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The designation "⌇⌇" or $$\begin{array}{cc} " & " \\ \xi & \xi \\ " & " \\ & \text{or} \end{array}$$

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

The terms pharmaceutically acceptable "salt" and "salts" may refer to basic salts formed with inorganic and organic bases. Such salts include ammonium salts; alkali metal salts, such as lithium, sodium, and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine, and the like; and zwitterions, the so-called "inner salts." Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid, or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic, or terephthalic acid, such as hydroxycarboxylic acids, for example ascorbic, glycolic, lactic, malic, tartaric, or citric acid, such as amino acids, (for example aspartic or glutamic acid or lysine or arginine), or benzoic acid, or with organic sulfonic acids, such as ($C_1$-$C_4$) alkyl or arylsulfonic acids, which are unsubstituted or substituted, for example by halogen, for example methanesulfonic acid or p-toluenesulfonic acid.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

Any compound that can be converted in vivo to provide the bioactive agent (i.e., the compound of formula I) is a prodrug within the scope and spirit of the invention.

The term "prodrug" denotes a compound which, upon administration to a subject, undergoes chemical conversion by metabolic or chemical processes to yield a compound of the formula, and/or a salt and/or solvate thereof. For example, compounds containing a carboxy group can form physiologically hydrolyzable esters which serve as prodrugs by being hydrolyzed in the body to yield formula compounds per se. Such prodrugs are preferably administered orally since hydrolysis in many instances occurs principally under the influence of the digestive enzymes. Parenteral administration may be used where the ester per se is active, or in those instances where hydrolysis occurs in the blood.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, Bundgaard, H. ed., Elsevier (1985);

c) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991); and d) Testa, B. et al., *Hydrolysis in Drug and Prodrug Metabolism*, Wiley-VCH (2003).

Said references are incorporated herein by reference.

Examples of physiologically hydrolyzable esters of compounds of formula (I) include $C_1$-$C_6$ alkylbenzyl, 4-methoxybenzyl, indanyl, phthalyl, methoxymethyl, $C_1$-$C_6$-alkanoyloxy-$C_1$-$C_6$-alkyl, e.g., acetoxymethyl, pivaloyloxymethyl, or propionyloxymethyl, $C_1$-$C_6$-alkoxycarbonyloxy-$C_1$-$C_6$-alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl, and other well known physiologically hydrolyzable esters used, for example, in the penicillin and cephalosporin arts. Such esters may be prepared by conventional techniques known in the art.

Prodrug ester examples include the following groups:

(1-alkanoyloxy)alkyl such as,

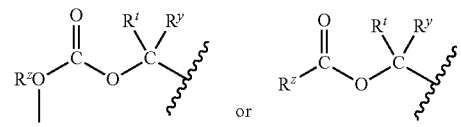

wherein $R^z$, $R^t$, and $R^y$ are H, alkyl, aryl, or arylalkyl; however, $R^zO$ cannot be HO.

Examples of such prodrug esters include

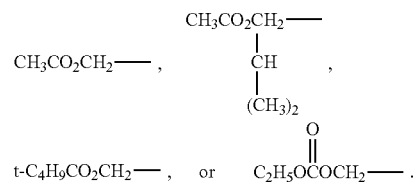

Other examples of suitable prodrug esters include

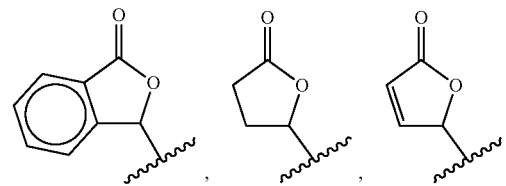

-continued

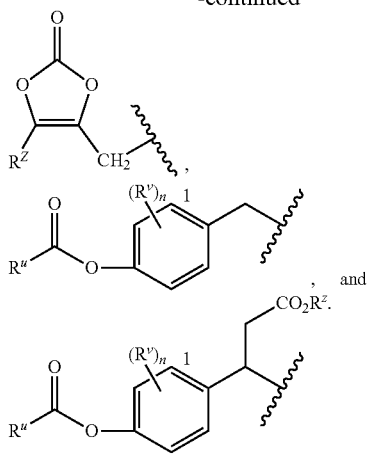

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl, or alkoxyl, and n1 is 0, 1, or 2.

The term "tautomer" refers to compounds of the formula I and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to treat or prevent diabetes and/or obesity.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The present invention is intended to include all isotopes of atoms occurring in the present compounds of the invention. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Synthesis

Compounds of formulae I may be prepared as shown in the following reaction schemes and the description thereof, as well as relevant literature procedures that may be used by one skilled in the art. Exemplary reagents and procedures for these reactions appear hereinafter and in the working Examples. Protection and deprotection in the Schemes below may be carried out by procedures generally known in the art (see, for example, Greene, T. W. et al., *Protecting Groups in Organic Synthesis*, 3rd Edition, Wiley (1999)).

The synthesis of biarylamine compounds of formula I is described in Scheme 1. The chloride of formula 1 can react with amine of formula 2 in several methods. 1. Direct nucleophilic substitution. Chloride 1 and amine 2 can be treated with a base such as potassium carbonate, cesium carbonate or sodium hydride in an inert solvent such as dimethyl formamide, tetrahydrofuran or dioxane at 40 to 200 degree for 1 to 72 hours to give the desired biaryl amine I. 2. Chloride 1 and amine 2 can react in the presence of a palladium catalyst such as palladium tetrakistriphenyl phonphine and a base such as triethyl amine or sodium bicarbonate in an inert solvent such as dimethyl formamide, tetrahydrofuran or dioxane at 40 to 200 degree for 1 to 72 hours to give the desired biaryl amine I.

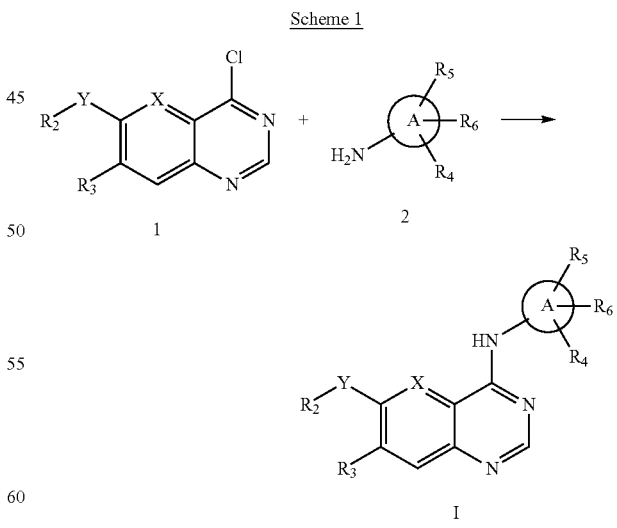

Scheme 1

Scheme 2 provides a general method to prepared chloride of formula 1 or 8. In particular, when X is CH, chloride of formula 8 can be readily prepared according to the literature. 2-Amino 5-hydroxybenzoic acid 3 can react with formaldehyde or equivalent to form 6-hydroxyquinazolin-4(1H)-one 4 in good yield (*Current Medicinal Chemistry*, 11(19):2549-2553 (2004); WO2003/064399; *Tetrahedron Letters*, 43(21): 3911-3913 (2002); *Journal of Medicinal Chemistry*, 26(3): 420-425) (1983). According to *Bioorganic & Medicinal Chemistry Letters*, 14(1): 111-114 (2004), 4 can then be converted to chloride 6 in good yields through acetate protection and chlorination with sulfonyl chloride. The acetate on chloride 6 can be deprotected with a base such as ammonia to provide alcohol 7. $R_2$ can be introduced to alcohol 7 through 1. a Mitsunobu reaction (*Synthesis*, 1 (1980)) or alkylation with $R_2$-halide with a base such as sodium hydride, potassium carbonate or cesium carbonate to form chloride 8.

Alternative synthesis of pertinent examples of chloride 1 or 8 can also be found in the patent application EP 1734040.

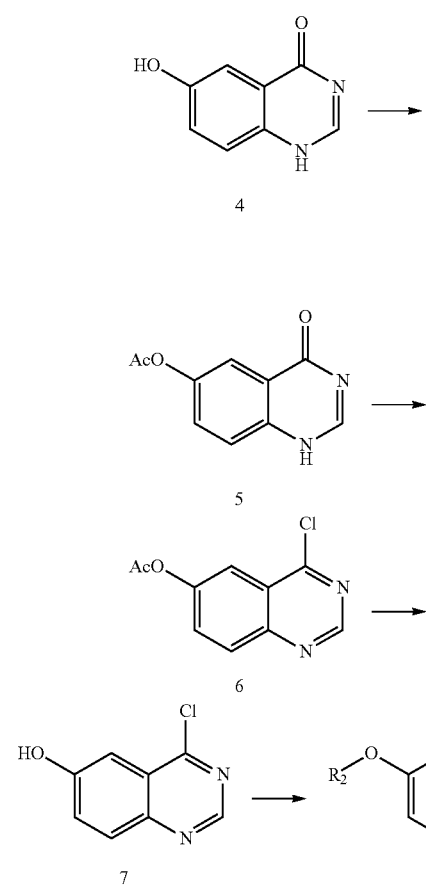

Procedures for the synthesis of pertinent examples of amine 2 are available in the literature (references include PCT International Applications WO 03/055482 and WO 04/002481; and Castellano et al., *Bioorg. Med. Chem. Lett.*, 15:1501 (2005)).

Scheme 3 describes a general approach to the synthesis of amine 2A wherein

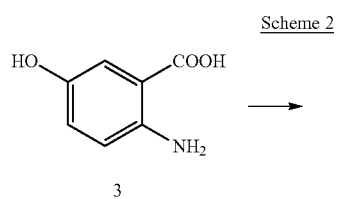

Z=bond m and n=0 i.e., where the resulting phosphonate group is directly attached to the heteroaromatic ring, $R_1$. A protected (pg) amino-substituted heteroaryl 9 with a suitably activated hydrogen substituent is deprotonated with a strong base such as LDA or n-butyllithium. PG refers to a protecting group such as Boc or Cbz. The resulting anion is reacted with a dialkylchlorophosphate 10 resulting in direct attachment of the phosphonate group to $R_1$. Removal of the protecting groups (PG) provides amine 2A. Alternatively, the halo-substituted heteroaryl 11 can also be converted to the same anionic intermediate via halogen-metal exchange by reaction with a base such as n-butyllithium. This approach can also be extended to the synthesis of phosphinic acids by the use of a reagent such as N,N-diethylchloromethylphosphonamide to react with the anion intermediate (Rumthao et al., *Bioorg. Med. Chem. Lett.*, 14:5165-5170 (2004)). As an example, the protected thiazole amine 12 may be deprotonated as shown in Scheme 3 using a base such as LDA or n-BuLi and phosphonylated as described to give, after deprotection, the 5-phosphonate-substituted thiazole amine 2B (South et al., *J. Het. Chem.*, 28:1017 (1991)).

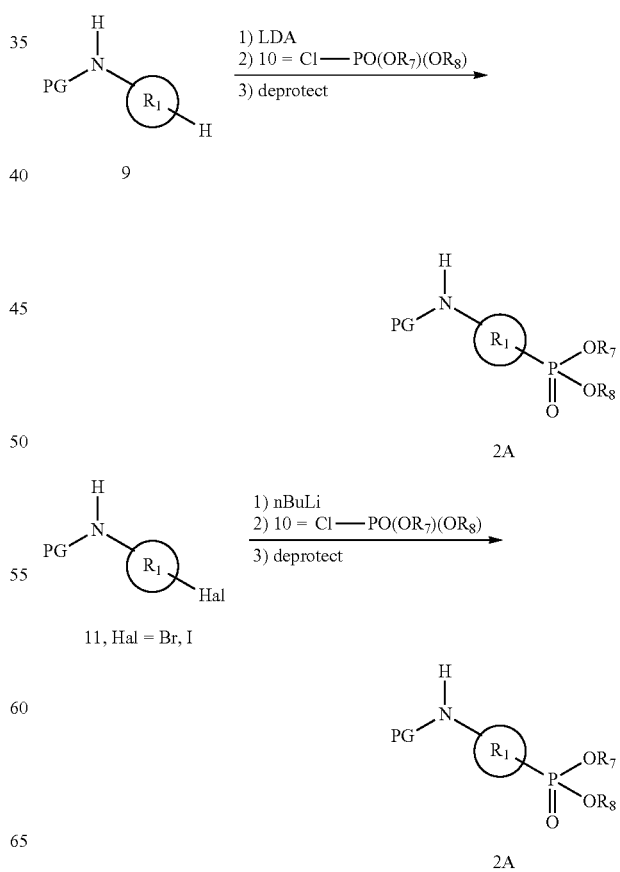

for example,

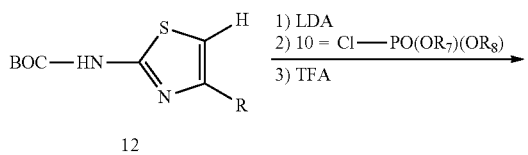

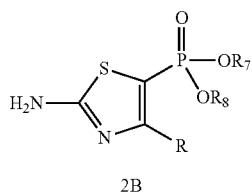

The reactions described in Scheme 3 above and Schemes 4, 5, 6, 7 and 8 below may also be conducted on compounds wherein quinazoline system has already been attached to the amine 2 and where the chemistry is allowed by compatible structure in the quinazoline system and/or the use of appropriate protecting groups.

Scheme 4 describes another approach to the synthesis of amine 2A. The protected (PG) heteroaryl amine 13 containing a substituent such as bromo, iodo or triflate is coupled to dialkylphosphite 14 in the presence of a catalytic amount of palladium(0) catalyst, such as tetrakis-triphenylphosphine palladium(0) to provide, after deprotection, the phosphonate substituted heteroaryl amine 2A (Hirao et al., *Synthesis*, 56-57 (1981)). The use of the reagent 15 in this reaction provides the corresponding phosphinate 2C (Rumthao et al., *Bioorg. Med. Chem. Lett.*, 14:5165-5170 (2004)). As an example, the reaction between the bromo pyridine 16 and dialkylphosphite 14 catalyzed by Pd(Ph$_3$P)$_4$ provides the phosphonylated pyridine compound I-A. Compound 16 is obtained by reacting chloride 1 to 5-bromo-2-aminopyrazine in the manner described in Scheme 1.

Scheme 4

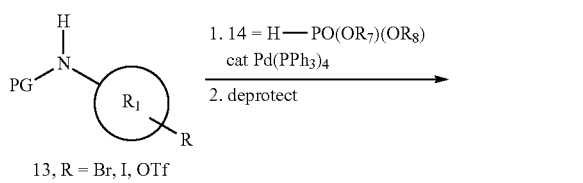

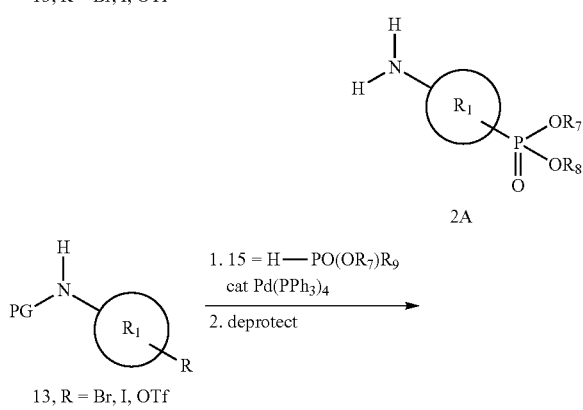

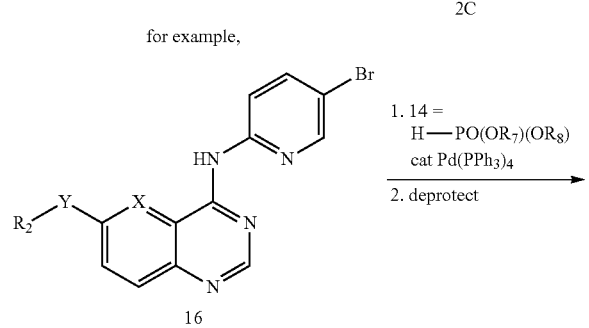

for example,

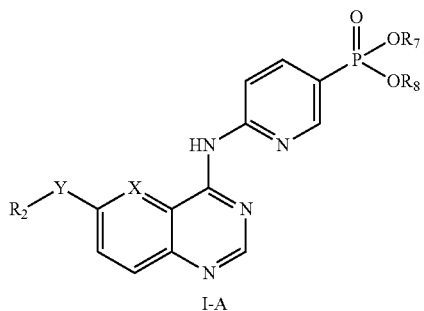

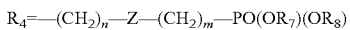

Scheme 5 describes the synthesis of compounds of formula I in which $R_4$=—(CH$_2$)$_n$—Z—(CH$_2$)$_m$—PO(OR$_7$)(OR$_8$)

Z=alkene or ethylene m and n=0 thus connecting the phosphonate group to the heteroaromatic ring with a two-carbon linker. A suitably protected heteroaryl amine 13 is coupled to vinyl phosphonate 17 in the presence of catalytic amounts of a Pd(II) catalyst such as Pd(OAc)$_2$ and phosphine ligand such as tri-o-tolylphosphine to give a protected vinyl phosphonate intermediate product (Xu et al., *Synthesis*, 556-558 (1983)). Removal of protecting groups yields the vinyl phosphonate amine 2D which is converted to I-B, the corresponding compound of formula I wherein Z=alkene (vinyl) by the manner described in Schemes 1 and 2. Hydrogenation in the presence of catalytic Pd(0) of 2D and I-B provides the corresponding ethylene (two-carbon) linked phosphonate compounds, 2E and 1-C. As mentioned earlier, these transformations can be conducted on a fully elaborated intermediate such as described conversion of aminopyrazine amide 16 to the vinyl phosphonate substituted pyrazine product I-D.

Scheme 5

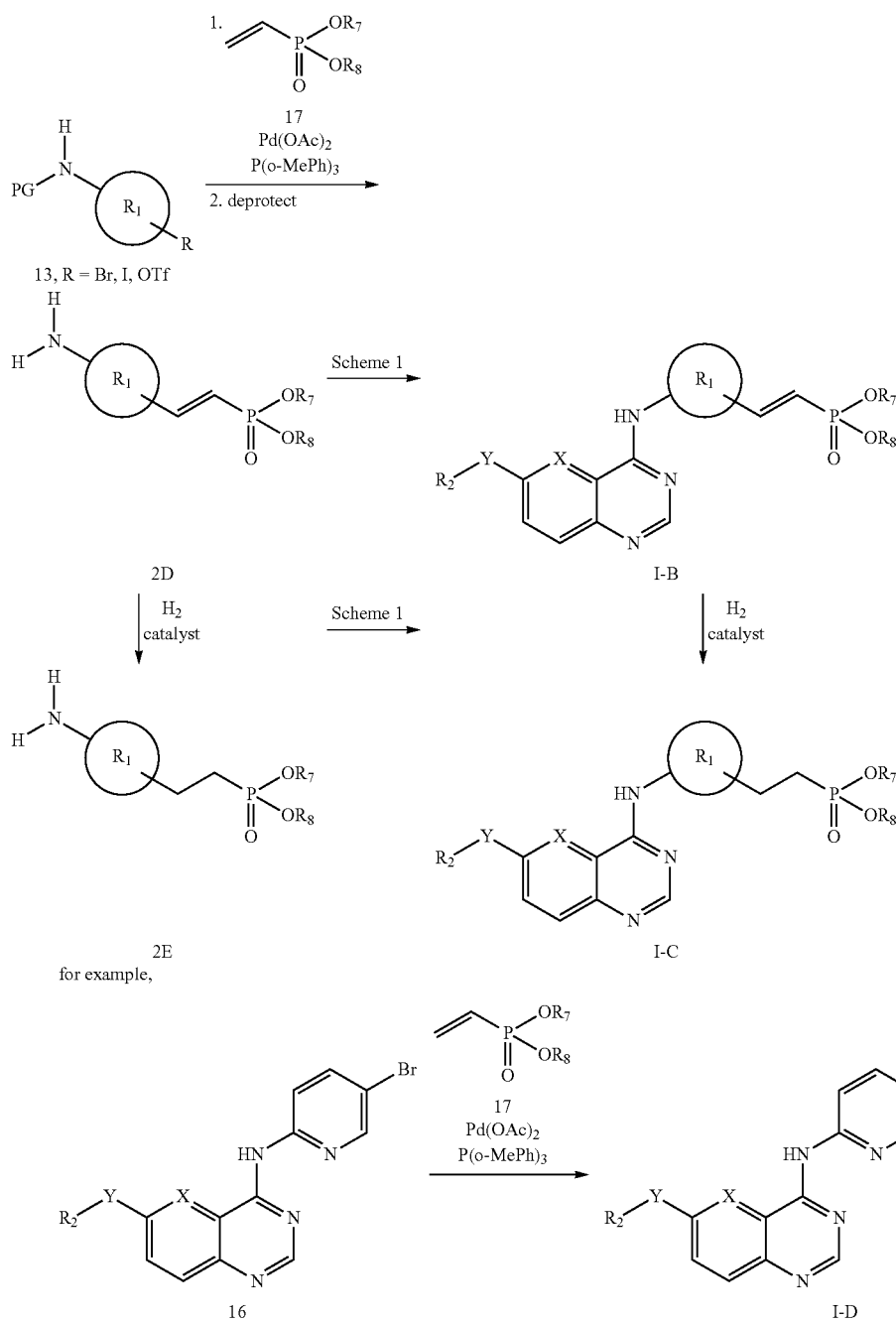

Scheme 6 describes the synthesis of compounds of formula I in which the phosphonate or phosphinate groups in $R_4$ are incorporated using the Arbusov (Engel, R., *Handbook of Organophosphorus Chemistry*, Marcel Dekker (1992)) or Michaelis-Becker (Engel, R., *Handbook of Organophosphorus Chemistry*, Marcel Dekker (1992)) reactions. In the Arbusov reaction, the alkyl halide 18 is heated with the trialkylphosphite 19 to yield, after removal of protecting groups, amine 2F. Amine 2F is converted to compounds of formula I-E by means described in Schemes 1. When carried out using $R_9P(OR_7)_2$ instead of the trialkylphosphite 19, the corresponding phosphinic ester product is obtained (i.e., where $R_4=-(CH_2)_n-Z-(CH_2)_m-PO-(R_9)(OR_7)$ (Kapustin et al., *Org. Lett.*, 5:3053-3057 (2003)). In the Michaelis-Becker reaction, compound 18 is reacted with dialkylphosphite 20 in the presence of base to yield, after removal of protecting groups, amine 2F. Amine 2F can be converted to compounds of formula I-E by means described in Schemes 1. As an example, the Boc-protected 5-bromomethylpyrazine 21 can heated with trialkylphosphite 19 to give, after removal of the Boc group, the phosphonomethyl-substituted pyrazine amine 2G, which can be converted to compounds of formula I as described above.

Scheme 6

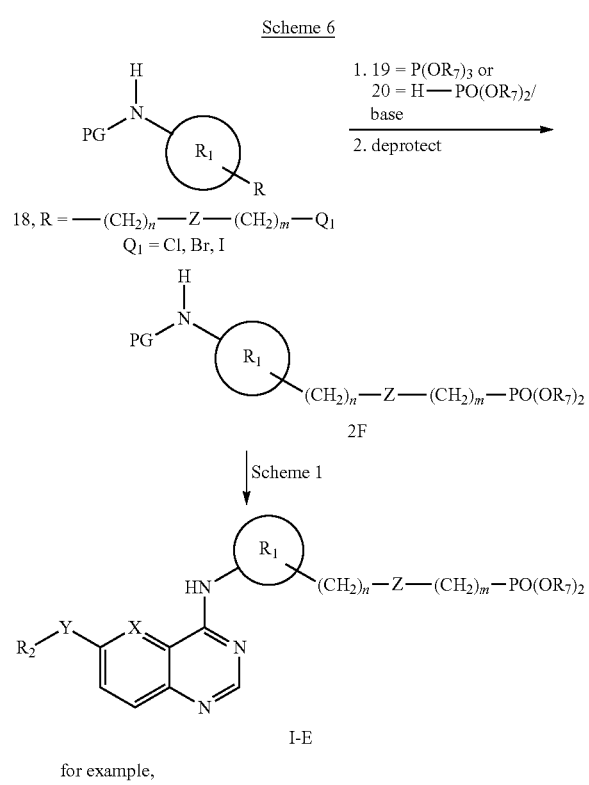

Scheme 7 describes the synthesis compounds of formula I in which the $R_1$ heteroaromatic ring is a thiazole. In this scheme, the phosphonate or phosphinate group in incorporated into an acyclic precursor prior to the formation of the heteroaromatic ring. In a standard Hantzsch thiazole synthesis, haloketone 22 is reacts with thiourea 23 to form the 4-substituted, 2-aminothiazole 2H. As an example, acetylphosphonic acid 24 is treated with bromine to form the α-haloketone 25. The reaction of 25 with thiourea 23 affords the 5-phosphono-2-aminothiazole 2I (Ohler et al., *Chem. Ber.*, 117:3034-3047 (1984)). The aminothiazoles 2H and 2I may be converted to compounds of formula I by means described in Scheme 1.

Scheme 7

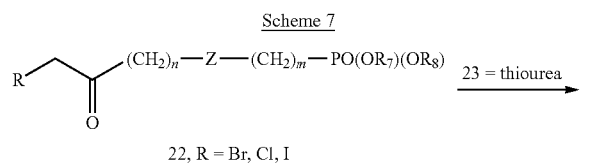

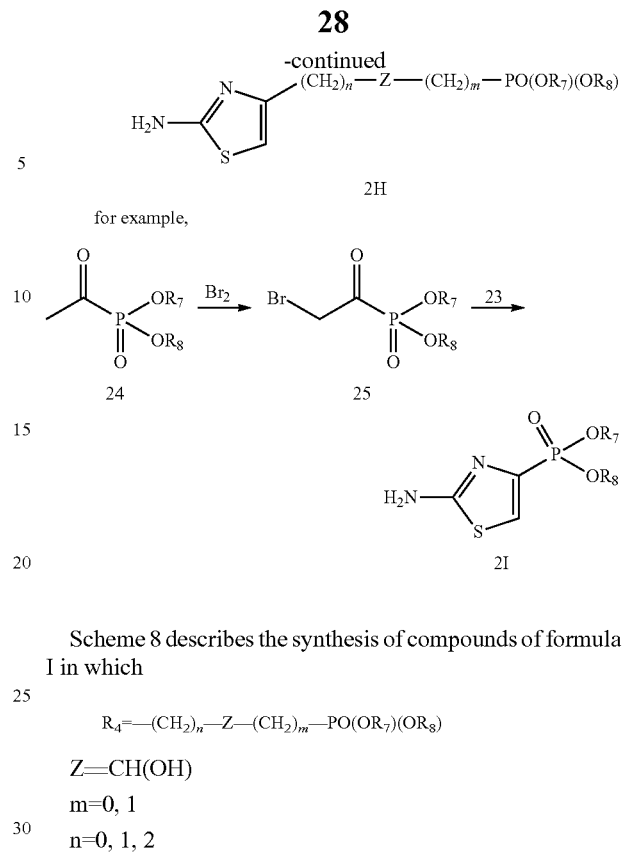

Scheme 8 describes the synthesis of compounds of formula I in which $R_4 = -(CH_2)_n - Z - (CH_2)_m - PO(OR_7)(OR_8)$ $Z = CH(OH)$ $m = 0, 1$ $n = 0, 1, 2$ i.e., compounds in which $R_4$ contains a hydroxy-substituted methylene [Z=CH(OH)] positioned between the heteroaromatic ring $R_1$ and the phosphonate group. In equation (1), reaction of dialkylphosphite 14 with aldehyde 26 in the presence of a base such as triethylamine or DBN gives the hydroxyphosphonate product I-F (Caplan et al., *J. Chem. Soc. Perkin* 1, 3:421-437 (2000)), representing a compound of formula I in which Z=CH(OH), n=0, 1, 2 and m=0. In equation (2), alkyl phosphonate 27 is treated with a base such as n-BuLi, followed by addition of aldehyde 26 gives the hydroxyphosphonate product I-G (Mikolajczyk et al., *Synthesis*, 691-694 (1984)), representing a compound of formula I in which Z=CH(OH), n=0, 1, 2 and m=1. As examples, the pyrazine 28 and thiazole 29 are converted as shown to the corresponding hydroxyphosphonates, I-H and I-I.

Scheme 8

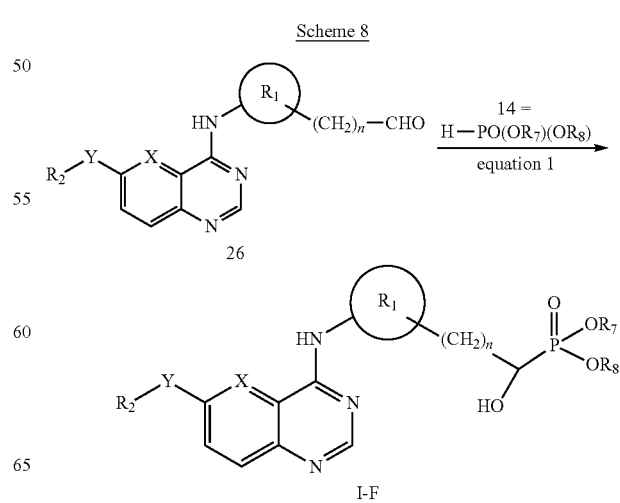

-continued

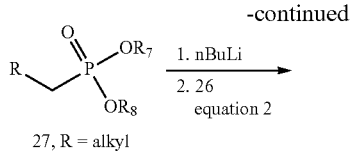

27, R = alkyl

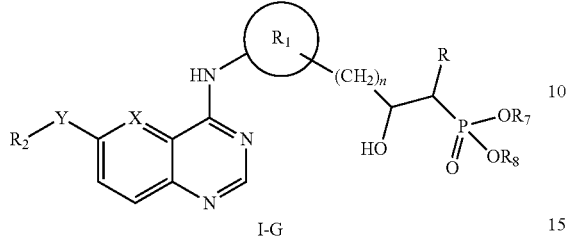

I-G for example,

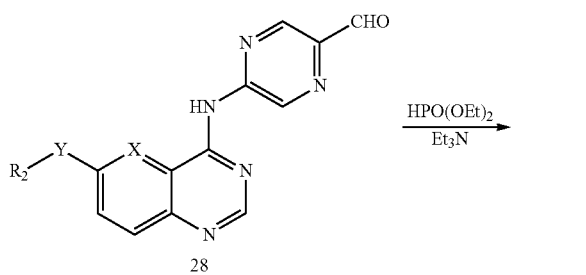

28

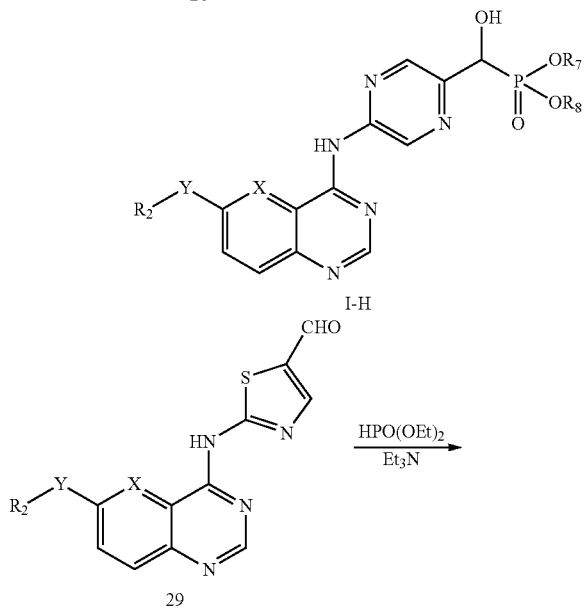

-continued

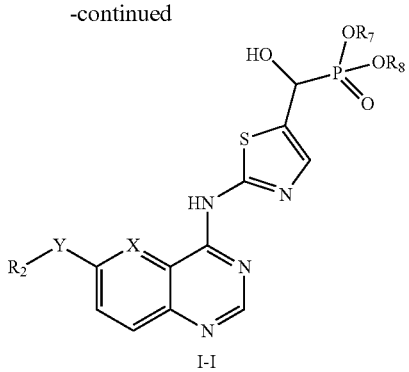

I-I

Scheme 9 describes the synthesis of compounds of formula I in which $R_4 = -(CH_2)_n-Z-(CH_2)_m-PO(OR_7)(OR_8)$ $Z = CH(OR_9)$ $m = 0$ $n = 0, 1, 2$ i.e., compounds in which $R_4$ contains a alkoxy-substituted methylene [$Z=CH(OR_9)$] positioned between the heteroaromatic ring $R_1$ and the phosphonate group. In equation (1), the hydroxyl phosphonate products I-F of Scheme 8 may be alkylated with suitable active alkyl halides 30 to give the alpha-alkoxy phosphonates I-J (Wrobleski et al., *Tetrahedron Asymmetry*, 13:845-850 (2002)). Alternatively, equation (2) depicts the rhodium-catalyzed insertion reaction of alcohols 32 with alpha-diazo phosphonates 31 which also provides compounds I-J (Cox, G. et al., *Tetrahedron*, 50:3195-3212 (1994); Moody, C. et al., *Tetrahedron Asymmetry*, 12:1657-1661 (2001)). The preparation of alpha-diazo phosphonates 31 has been described by direct diazo transfer to the corresponding ketone 33 (Regitz, M., *Tetrahedron Lett.*, 9:3171-3174 (1968)). Alternatively, the diazo phosphonates 31 can be obtained via base-catalyzed decomposition of the alpha-toluenesulfonylhydrazides derived from the corresponding keto phosphonates 33 (Marmor, R. et al., *J. Org. Chem.*, 36:128-136 (1971)). The alpha-keto phosphonates 33 may be synthesized directly from alpha-hydroxy phosphonates (I-F) by oxidation using a reagent such as $CrO_3$ (Kaboudin, B. et al., *Tetrahedron Lett.*, 41:3169-2171 (2000)). Alternatively, the Arbusov reaction between an acid chloride and trialkylphosphite yields the corresponding alpha-keto phosphonate (Marmor, R., et al., *J. Org. Chem.*, 36:128-136 (1971)).

Scheme 9

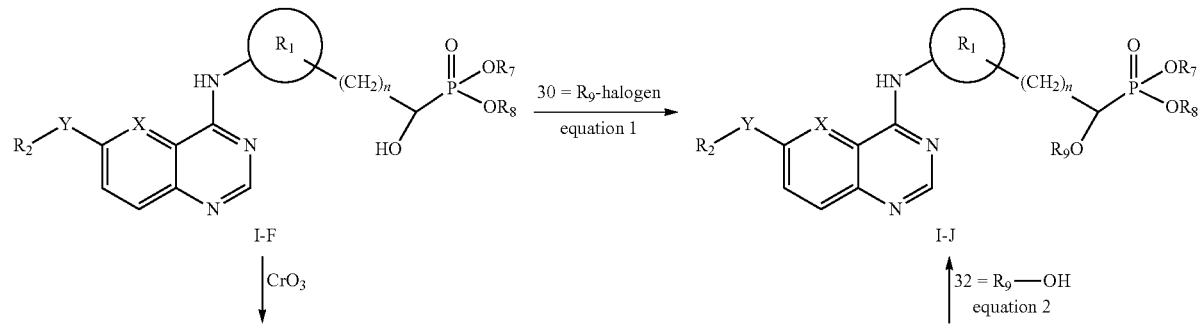

31  32

-continued

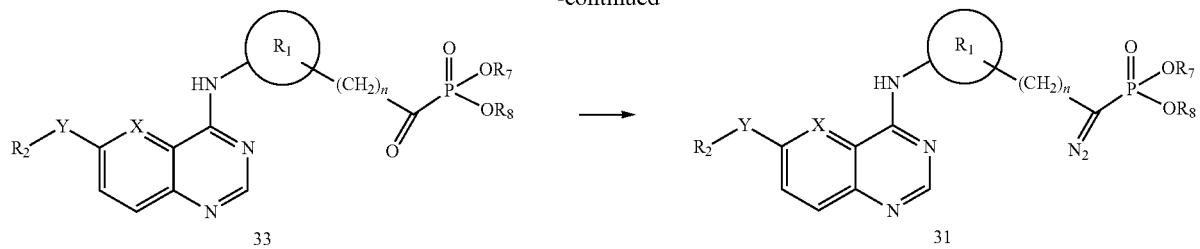

Scheme 10 describes the synthesis of compounds of formula I in which $R_4=-(CH_2)_n-Z-(CH_2)_m-PO(OR_7)(OR_8)$
$Z=CH(NHR_9)$
$m=0$
$n=0, 1, 2$ i.e., compounds in which $R_4$ contains an amino-substituted methylene [$Z=CH(NHR_9)$] positioned between the heteroaromatic ring $R_1$ and the phosphonate group. In Scheme 10, aldehyde 26 can be reacted with a dialkylphosphite 14 and amine 34 to give the alpha-amino substituted phosphonate I-K by conducting the reaction in the presence of silica gel and microwave irradiation (Zhan et al., *Chem. Lett.*, 34:1042-1043 (2005)). Other methods involve preformation of the corresponding imine resulting from condensation of the aldehyde 26 and amine 34, which is followed by reaction with the dialkylphosphite 14 in the presence of various catalysts such as Lewis acids (Laschat et al., *Synthesis*, 90 (1992)). Furthermore, other catalysts may be used for the one-pot synthesis described in Scheme 10 (for example, use of $SmI_2$ is described in Xu et al., *Eur. J. Org. Chem.*, 4728 (2003)).

Scheme 10

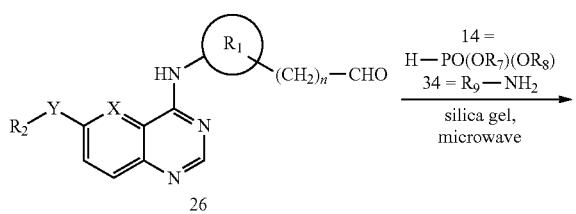

-continued

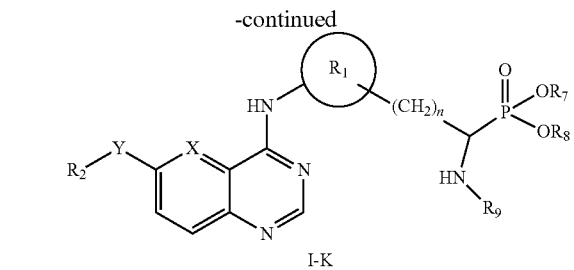

I-K

Scheme 11 describes the synthesis of compounds of formula I in which $R_4=-(CH_2)_n-Z-(CH_2)_m-O-PO(OR_7)R_9$ and $-(CH_2)_nZ-(CH_2)_m-O-PO-R_9R_{10}$.

Reaction of the alcohol precursor 35 with the a phosphonyl chloride 36 or phosphinyl chloride 37 in the presence of a base such as pyridine or triethylamine yields the phosphonate compound I-L (equation 1) or the phosphinate compound I-M (equation 2). In addition to the reaction shown for the synthesis of phosphonates I-L, other methods include the direct esterification of a phosphonic acid or the use of the Mitsunobu reaction (Saady et al., *Tetrahedron Lett.*, 36:2239-2242 (1995)). The preparation of phosphinic esters of dimethylphosphinic acid (I-M wherein $R_9$ and $R_{10}$=Me) has been described using dimethylphosphinyl chloride and tetrazole in the presence of pyridine to produce an intermediate phosphinyl tetrazolide (PCT International Application WO 00/078763).

Scheme 11

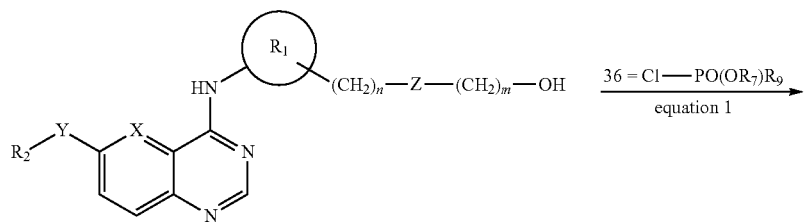

equation 1

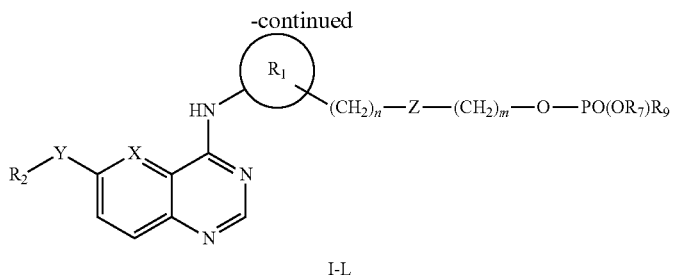

I-L

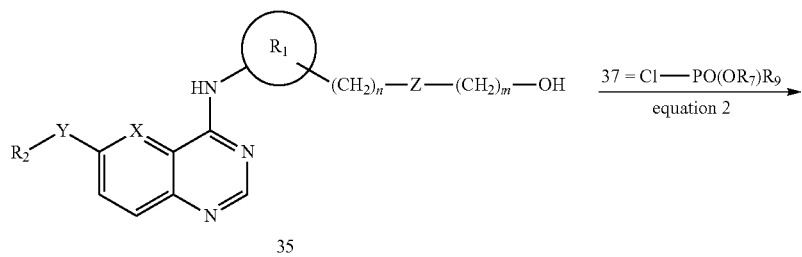

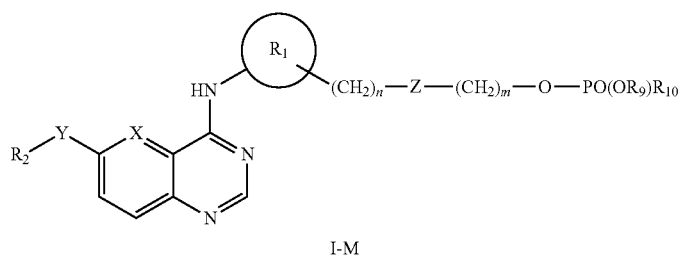

I-M

Scheme 12 describes the synthesis of compounds of formula I in which

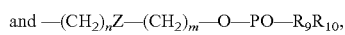

and Z=S or $SO_2$,
and m=1 or 2,
and n=0, 1 or 2.

Reaction of a suitably activated halogen-substituted heteroaromatic intermediate 13 with potassium thiocyanate gives the thiocyanate intermediate 38. At this point, protecting groups may be removed and the resulting amino heteroaromatic compound can react with chloride 1 to give intermediate 39. Treatment of thiocyanate 39 with $NaBH_4$ yields the corresponding thiol intermediate which is alkyated with the substituted halide 40 to give compounds of formula I wherein Z=S (I-N). Treatment of the product I-N with oxidizing agents such as hydrogen peroxide or OXONE® gives compounds of formula I wherein Z=$SO_2$ (I-O). As an example, treatment of the HBr salt of 2-amino-5-bromothiazole 41 with, for instance, potassium thiocyanate, affords thiocyanate 42. The amino-thiocyanate product reacts with chloride 1 using standard means to give the amide 43. Reduction of the thiocyanate group of 43 with a reagent such as $NaBH_4$, followed by alkylation of the resulting free thiol with iodomethyl phosphonate 44 gives phosphonate compounds of formula I where Z=S, m=1 and n=0 (I-N).

Scheme 12

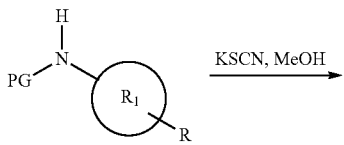

13, R = Br, I, OTf

-continued
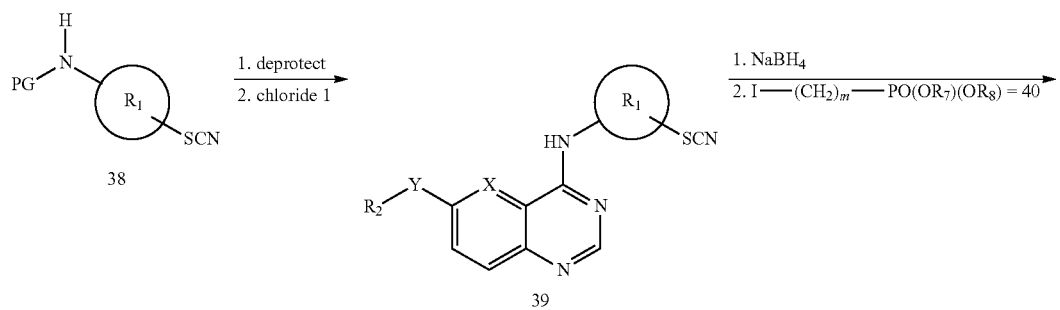
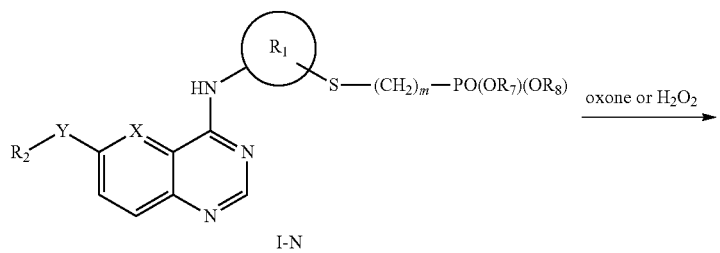
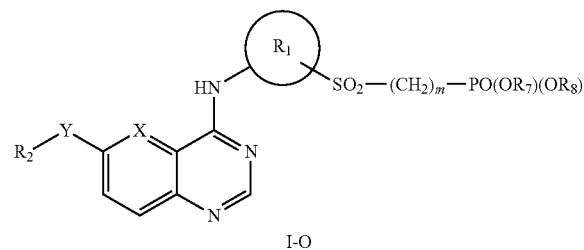
for example,
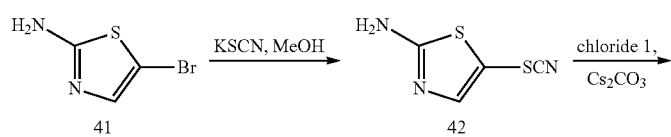
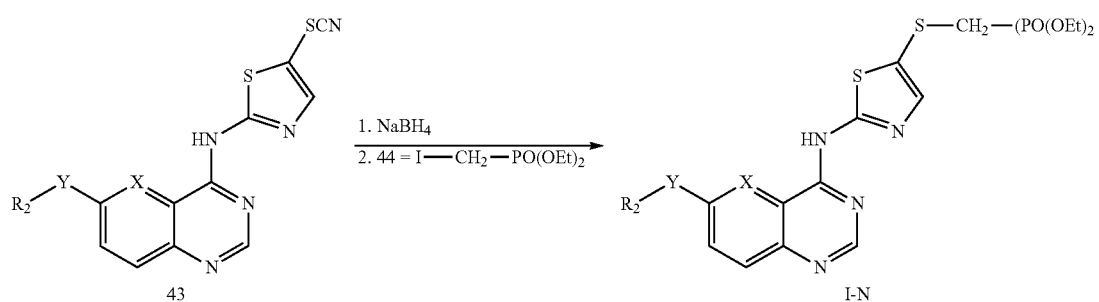

Scheme 13 describes the synthesis of compounds of formula I in which

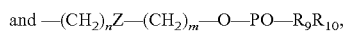

and Z=O,
and m=1 or 2,
and n=0, 1 or 2.

Reaction of a suitably activated halogen-substituted heteroaromatic intermediate 45 with the hydroxy substituted phosphonate intermediate 46 in the presence of silver oxide yields I-P, the phosphonate compound of formula I in which Z=O, m=1 or 2, and n=0, 1 or 2 (Flor et al., *J. Med. Chem.*, 1999, 42:2633-2640).

Scheme 14

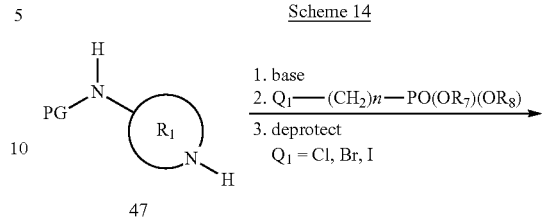

Scheme 13

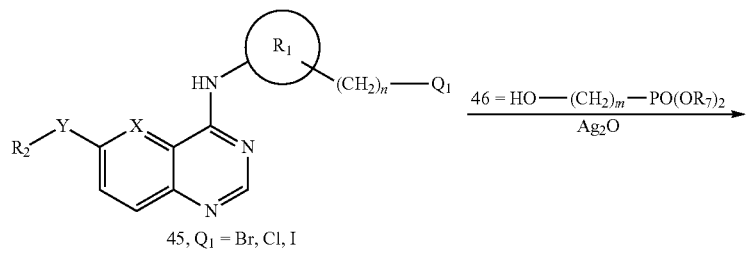

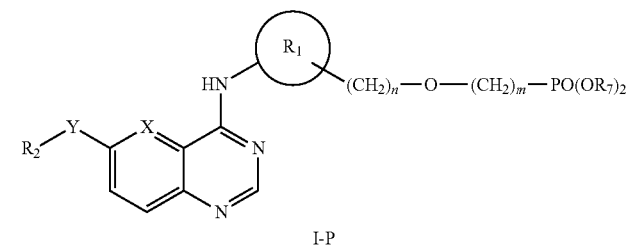

I-P

Scheme 14 describes a general synthesis of amine 2J, where the phosphonate or phosphinate moiety (here illustrated by a phosphonate) is linked to the heterocycle $R_1$ by a nitrogen atom rather than a carbon atom. A protected (Pro) amino-heterocycle such as 47 can be deprotonated with a base followed by alkylation with an appropriate halide containing the phosphonate/phosphinate moiety followed by deprotection to give amine 2J. This is illustrated by the example of the N-Boc protected triazole 48, which is deprotonated with a base (e.g., NaH), then alkylated with an iodomethyl phosphonate 49. Deprotection of the N-Boc group then furnishes the aminotriazole phosphonate 50. On the other hand, in certain cases, the amino-heterocycle does not need to be protected, as illustrated in the case of the pyrazole 51, which can be deprotonated with a base such as KOtBu and alkylated preferentially on the ring nitrogen with electrophiles such as an iodomethyl phosphonate 49 to form product 52.

-continued

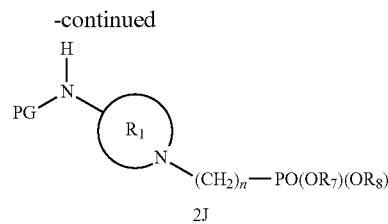

for example,

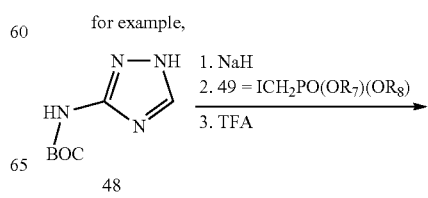

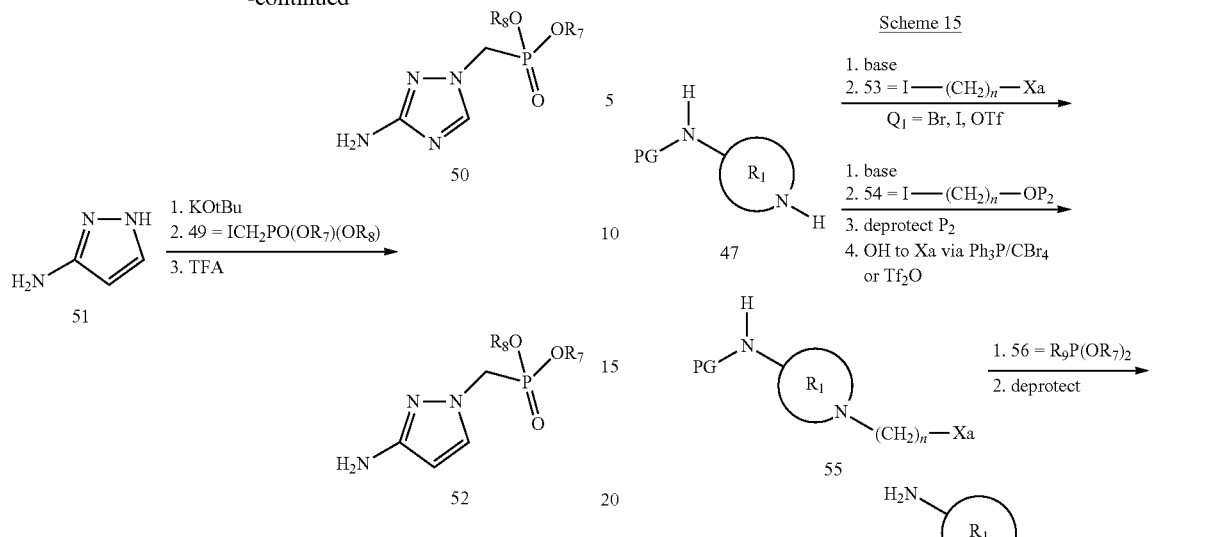

An alternative representative approach to N-alkylated phosphonates/phosphinates is shown in Scheme 15. Amine 47 can be deprotonated with an appropriate base and reacted with an iodide such as 53 (containing a functional group Xa, e.g., Cl, Br, OTs) to give the N-alkylated heterocycle 55. Alternatively, amine can be reacted with an iodide such as 54 (containing e.g., a protected hydroxyl group $OP_2$, which can subsequently be deprotected and converted to a halide via known methods, e.g., $Ph_3P/CBr_4$) to provide the N-alkylated heterocycle 55. This intermediate then can be reacted with either a trialkyl phosphate (Arbusov reaction) as described in Scheme 6 to provide a phosphonate, or, as shown here. When halide 55 is reacted with the phosphonite 56, the product is the corresponding phosphinic ester 2K (reference: Kapustin et al., *Org. Lett.*, 5:3053-3057 (2003)).

Scheme 16 describes the synthesis of compounds of formula 2L which contain cyclic phosphonate esters. The phosphonate diester of intermediate amine 2F is protected (e.g., as a tert-butyl carbamate or as a benzyl carbamate) to give the phosphonate 57, which is dealkylated with an agent such as bromotrimethylsilane. The resulting bis-trimethylsilyl phosphonic acid ester is reacted directly with oxalyl chloride to give the phosphoryl dichloride 58. Intermediate 58 is converted to the desired cyclic phosphonate 2L by reaction with an appropriate diol 59 in the presence of a base (reference: Notter et al., *Bioorg. Med. Chem. Lett.*, 17:113-117 (2007)), followed by deprotection.

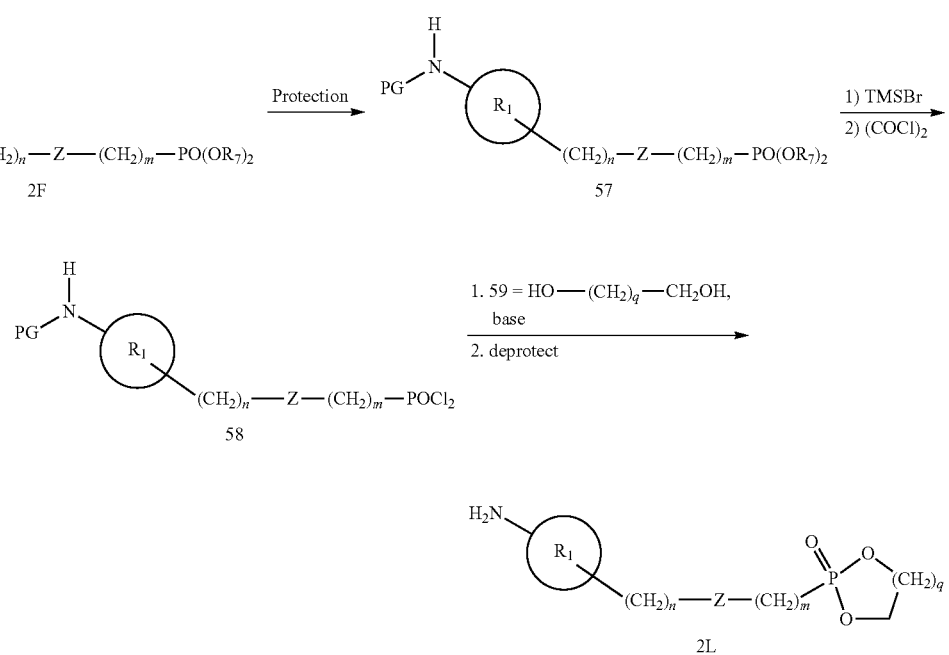

Similarly, Scheme 17 describes the synthesis of compounds of formula 2M which contain cyclic phosphine oxides. The phosphoryl dichloride 58 can be reacted with a Grignard reagent formed from a dibromide 60 and magnesium, followed by deprotection to provide the cyclic phosphine oxide 2M (reference: Polniaszek, R. et al., *J. Org. Chem.*, 56:3137-3146 (1991)).

Scheme 17

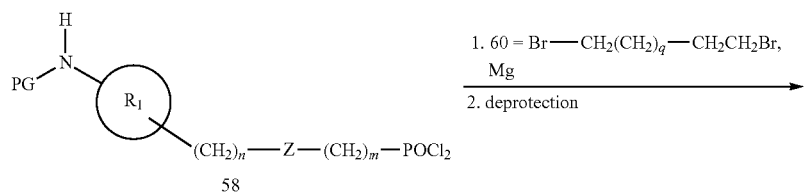

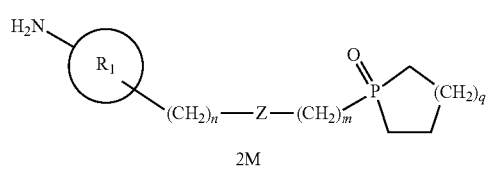

Scheme 18 describes the synthesis of compounds of formula I-Q which contain cyclic phosphinates. Ethyl dichlorophosphate is reacted with a Grignard reagent formed from a dibromide 60 and magnesium to give the cyclic phosphinate ester 61 (reference: Polniaszek, R. et al., *J. Org. Chem.*, 56:3137-3146 (1991)). Ester 61 is dealkylated (e.g., with bromotrimethylsilane) and the resulting trimethylsilyl phosphonic acid ester is reacted directly with a chlorinating agent (e.g., oxalyl chloride) to give the phosphoryl chloride 62, which is then reacted with alcohol 35 in the presence of a base to give compounds of formula I-Q.

Scheme 18

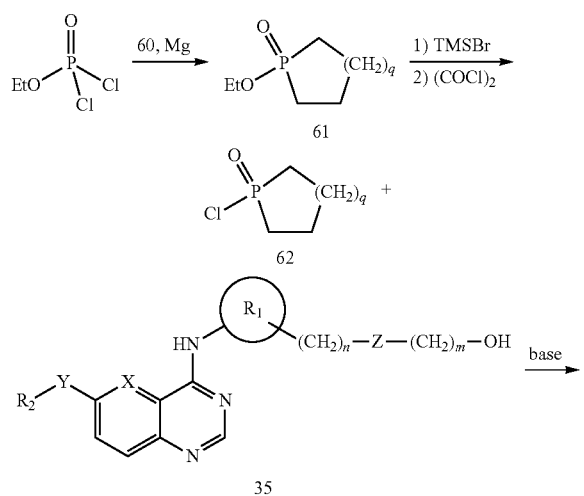

-continued

Utilities and Combinations

A. Utilities

The compounds of the present invention possess activity as enhancers of activity of the enzyme glucokinase, and, therefore, may be used in the treatment of diseases associated with glucokinase activity.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, and other maladies. Consequently, it is believed that the compounds of the present invention may be used in preventing, inhibiting, or treating diabetes, especially Type II diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, and glaucoma.

Metabolic Syndrome or "Syndrome X" is described in Ford et al., *J. Am. Med. Assoc.*, 287:356-359 (2002) and Arbeeny et al., *Curr. Med. Chem.—Imm., Endoc. &Metab. Agents*, 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other enhancers of activity of glucokinase or one or more other suitable therapeutic agents useful in the treatment of the aforementioned disorders including: antidiabetic agents, anti-hyperglycemic agents, anti-hyperinsulinemic agents, anti-retinopathic agents, anti-neuropathic agents, anti-nephropathic agents, anti-atherosclerotic agents, anti-infective agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-ischemic agents, anti-cancer agents, anti-cytotoxic agents, anti-restenotic agents, anti-pancreatic agents, lipid lowering agents, appetite suppressants, memory enhancing agents, and cognitive agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones (PPARgamma agonists): ciglitazone, pioglitazone, troglitazone, rosiglitazone; non-thiazolidinedione PPAR-gamma agonists; selective PPARgamma modulators (SPPARMs; e.g., metaglidasen from Metabolex); PPAR-alpha agonists; PPAR alpha/gamma dual agonists; PPAR delta agonists, PPARalpha/gamma/delta pan agonists; SGLT2 inhibitors; dipeptidyl peptidase-IV (DPP4) inhibitors; aldose reductase inhibitors; RXR agonists: JTT-501, MX-6054, DRF2593, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's farglitazar (GI-262570), englitazone (CP-68722, Pfizer), or darglitazone (CP-86325, Pfizer), isaglitazone (MIT/J&J), JTT-501 (JPNT/P&U), L-895645 (Merck), R-119702 (Sankyo/WL), NN-2344 or balaglitazone (Dr. Reddy/NN), or YM-440 (Yamanouchi).

Suitable PPAR alpha/gamma dual agonists include muraglitazar (Bristol-Myers Squibb), tesaglitazar (Astra/Zeneca), naveglitazar (Lilly/Ligand); AVE-0847 (Sanofi-Aventis); TAK-654 (Takeda), as well as those disclosed by Murakami et al., "A Novel Insulin Sensitizer Acts As a Coligand for Peroxisome Proliferation-Activated Receptor Alpha (PPAR alpha) and PPAR gamma; Effect of PPAR alpha Activation on Abnormal Lipid Metabolism in Liver of Zucker Fatty Rats", *Diabetes*, 47:1841-1847 (1998), WO 01/21602 and U.S. Pat. No. 6,414,002, the disclosure of which is incorporated herein by reference, employing dosages as set out therein, which compounds designated as preferred are preferred for use herein. Suitable PPARdelta agonists include, for example, GW-501516 (Glaxo). Suitable PPARalpha/gamma/delta pan agonists include, for example, GW-677954 (Glaxo).

Suitable alpha2 antagonists also include those disclosed in WO 00/59506, employing dosages as set out herein.

Suitable SGLT2 inhibitors include dapagliflozin (Bristol-Myers Squibb), T-1095, phlorizin, WAY-123783, and those described in WO 01/27128.

Suitable DPP4 inhibitors include saxagliptin (Bristol-Myers Squibb), vildagliptin (Novartis), alogliptin (Takeda) and sitagliptin (Merck) as well as those disclosed in WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., *Biochemistry*, 38(36): 11597-11603 (1999), TSL-225 (tryptophyl-1,2,3,4-tetrahydroisoquinoline-3-carboxylic acid) as disclosed by Yamada et al., *Bioorg. & Med. Chem. Lett.*, 8:1537-1540 (1998), 2-cyanopyrrolidides and 4-cyanopyrrolidides, as disclosed by Ashworth et al., *Bioorg. & Med. Chem. Lett.*, 6(22):1163-1166 and 2745-2748 (1996), employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1 (1-36) amide, GLP-1 (7-36) amide, GLP-1 (7-37) (as disclosed in U.S. Pat. No. 5,614,492 to Habener), as well as AC2993 (Amylin), liraglutide (Novo Nordisk) and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, cholesterol ester transfer protein inhibitors (e.g., torcetrapib (Pfizer)), and/or nicotinic acid and derivatives thereof.

MTP inhibitors which may be employed as described above include those disclosed in U.S. Pat. Nos. 5,595,872, 5,739,135, 5,712,279, 5,760,246, 5,827,875, 5,885,983, and 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440; and related statin compounds disclosed in U.S. Pat. No. 5,753,675; pyrazole analogs of mevalonolactone derivatives, as disclosed in U.S. Pat. No. 4,613,610; indene analogs of mevalonolactone derivatives, as disclosed in PCT application WO 86/03488; 6-[2-(substituted-pyrrol-1-yl)alkyl)pyran-2-ones and derivatives thereof, as disclosed in U.S. Pat. No. 4,647,576; Searle's SC-45355 (a 3-substituted pentanedioic acid derivative) dichloroacetate; imidazole analogs of mevalonolactone, as disclosed in PCT application WO 86/07054; 3-carboxy-2-hydroxy-propane-phosphonic acid derivatives, as disclosed in French Patent No. 2,596,393; 2,3-disubstituted pyrrole, furan and thiophene derivatives, as disclosed in European Patent Application No. 0221025; naphthyl analogs of mevalonolactone, as disclosed in U.S. Pat. No. 4,686,237; octahydronaphthalenes, such as disclosed in U.S. Pat. No. 4,499,289; keto analogs of mevinolin (lovastatin), as disclosed in European Patent Application No. 0142146 A2; and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin, and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al., J. Med. Chem., 31(10):1869-1871 (1988), including isoprenoid (phosphinyl-methyl)phosphonates, as well as other known squalene synthetase inhibitors, for example, as disclosed in U.S. Pat. Nos. 4,871,721 and 4,924,024 and in Biller, S. A., et al., Current Pharmaceutical Design, 2:1-40 (1996).

In addition, other squalene synthetase inhibitors suitable for use herein include the terpenoid pyrophosphates disclosed by Ortiz de Montellano, P. et al., J. Med. Chem., 20:243-249 (1977), the farnesyl diphosphate analog A and presqualene pyrophosphate (PSQ-PP) analogs as disclosed by Corey et al., J. Am. Chem. Soc., 98:1291-1293 (1976), phosphinylphosphonates reported by McClard, R. W. et al, J. Am. Chem. Soc., 109:5544 (1987) and cyclopropanes reported by Capson, T. L., Ph.D. dissertation, June, 1987, Dept. Med. Chem. U. of Utah, Abstract, Table of Contents, pp. 16, 17, 40-43, 48-51, Summary.

The fibric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, probucol and gemfibrozil being preferred, bile acid sequestrants, such as cholestyramine, colestipol and DEAE-SEPHADEX® (SECHOLEX®, Policexide), as well as LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future, 24:9-15 (1999), (Avasimibe); Nicolosi et al, "The ACAT inhibitor, C1-1011 is effective in the prevention and regression of aortic fatty streak area in hamsters", Atherosclerosis (Shannon, Irel.), 137(1): 77-85 (1998); Ghiselli, G., "The pharmacological profile of FCE 27677: a novel ACAT inhibitor with potent hypolipidemic activity mediated by selective suppression of the hepatic secretion of ApoB 100-containing lipoprotein", Cardiovasc. Drug Rev., 16(1):16-30 (1998); Smith, C., et al, "RP 73163: a bioavailable alkylsulfinyl-diphenylimidazole ACAT inhibitor", Bioorg. Med. Chem. Lett., 6(1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", Curr. Med. Chem., 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl] ureas with enhanced hypocholesterolemic activity", Chemtracts: Org. Chem., 8(6):359-362 (1995), or TS-962 (Taisho Pharmaceutical Co. Ltd.).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitors for use in combination with the compounds of the invention include SCH48461 (Schering-Plough), as well as those disclosed in Atherosclerosis, 115:45-63 (1995) and J. Med. Chem., 41:973 (1998).

Examples of suitable ileal Na+/bile acid cotransporter inhibitors for use in combination with the compounds of the invention include compounds as disclosed in Drugs of the Future, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al, "15-Lipoxygenase and its Inhibition: A Novel Therapeutic Target for Vascular Disease", *Current Pharmaceutical Design*, 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, and those discussed in Hertzog, D. L., *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer,) or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson), or AXOKINE® (Regeneron), with sibutramine and topiramate being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (TAXOL®), docetaxel (Taxotere), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators; and monoclonal antibodies. Additional anti-cancer agents are disclosed in EP 1177791. The compounds of the invention may also be used in conjunction with radiation therapy.

Examples of suitable memory enhancing agents, anti-dementia agents, or cognitive agents for use in combination with the compounds of the present invention include, but are not limited to, donepezil, rivastigmine, galantamine, memantine, tacrine, metrifonate, muscarine, xanomelline, deprenyl, and physostigmine.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the compound of Formula I of the invention for a human adult can be selected from the oral dose range of 0.01 to 30 mg/kg body weight (preferably 0.05 to 10 mg/kg body weight, more preferably 0.05 to 5 mg/kg body weight) or the clinical dose range of 0.005 to 10 mg/kg body weight (preferably 0.01 to 10 mg/kg body weight, more preferably 0.01 to 1 mg/kg body weight) or 0.5 to 1000 mg/day, preferably 1 to 500 mg/day. The other active component or components having different modes of action for use in combination can also be used in dose ranges selected by referring to the respective recommended clinical dose ranges. Administration is generally carried out in a single dose/day or in divided doses, for example, 2 to 4 times a day.

Abbreviations

The following abbreviations are employed in the Examples and elsewhere herein:

| | |
|---|---|
| Ph = | phenyl |
| Bn = | benzyl |
| t-Bu = | tertiary butyl |
| i-Bu = | iso-butyl |
| Me = | methyl |
| Et = | ethyl |
| Pr = | propyl |
| iPr = | isopropyl |
| Bu = | butyl |
| AIBN = | 2,2'-Azobisisobutyronitrile |
| TMS = | trimethylsilyl |
| TMSCHN$_2$ = | (trimethylsilyl)diazomethane |
| TMSN$_3$ = | trimethylsilyl azide |
| TBS = | tert-butyldimethyl |
| FMOC = | fluorenylmethoxycarbonyl |
| Boc or BOC = | tert-butoxycarbonyl |
| Cbz = | carbobenzyloxy or carbobenoxy or benzyloxycarbonyl |
| THF = | tetrahydrofuran |
| Et$_2$O = | diethyl ether |
| hex = | hexanes |
| EtOAc = | ethyl acetate |
| DMF = | dimethyl formamide |
| MeOH = | methanol |
| EtOH = | ethanol |
| DCM = | dichloromethane |
| i-PrOH = | isopropanol |
| DMSO = | dimethyl sulfoxide |
| DME = | 1,2 dimethoxyethane |
| DMA = | N,N-dimethylacetylamide |
| DCE = | 1,2 dichloroethane |
| HMPA = | hexamethyl phosphoric triamide |
| HOAc or AcOH = | acetic acid |
| TFA = | trifluoroacetic acid |
| DIEA or DIPEA or i-Pr$_2$NEt or Hunig's Base = | diisopropylethylamine |
| TEA or Et$_3$N = | triethylamine |
| NMM = | N-methyl morpholine |
| NBS = | N-bromosuccinimide |
| NCS = | N-chlorosuccinimide |
| DMAP = | 4-dimethylaminopyridine |
| DEPBT = | 3-diethoxyphosphoryloxy-1,2,3-benzotriazin-4[3H]-one |
| mCPBA = | 3-chloroperoxybenzoic acid |
| NaBH$_4$ = | sodium borohydride |
| NaBH(OAc)$_3$ = | sodium triacetoxyborohydride |
| NaN$_3$ = | sodium azide |
| DIBALH = | diisodium aluminium hydride |

| | |
|---|---|
| LiAlH₄ = | lithium aluminum hydride |
| n-BuLi = | n-butyllithium |
| OXONE® = | monopersulfate |
| Pd/C = | palladium on carbon |
| PXPd₂ = | Dichloro(chlorodi-tert-butylphosphine)palladium (II) dimer or [PdCl₂(t-Bu)₂PCl]₂ |
| PtO₂ = | platinum oxide |
| KOH = | potassium hydroxide |
| NaOH = | sodium hydroxide |
| LiOH = | lithium hydroxide |
| LiOH•H₂O = | lithium hydroxide monohydrate |
| HCl = | hydrochloric acid |
| H₂SO₄ = | sulfuric acid |
| H₂O₂ = | hydrogen peroxide |
| Al₂O₃ = | aluminum oxide |
| K₂CO₃ = | potassium carbonate |
| Cs₂CO₃ = | cesium carbonate |
| NaHCO₃ = | sodium bicarbonate |
| ZnBr₂ = | zinc bromide |
| MgSO₄ = | magnesium sulfate |
| Na₂SO₄ = | sodium sulfate |
| KSCN = | potassium thiocyanate |
| NH₄Cl = | Ammonium chloride |
| DBU = | 1,8-diazabicyclo[5.4.0]undec-7-ene |
| EDC (or EDC•HCl) or EDCI (or EDCI•HCl) or EDAC = | 3-ethyl-3'-(dimethylamino)propyl-carbodiimide hydrochloride (or 1-(3-dimethylaminopropyl)-3-ethylcarbodiimide hydrochloride) |
| HOBT or HOBT•H₂O = | 1-hydroxybenzotriazole hydrate |
| HOAT = | 1-Hydroxy-7-azabenzotriazole |
| PyBOP reagent or BOP reagent = | benzotriazol-1-yloxy-tris (dimethylamino) phosphonium hexafluorophosphate |
| NaN(TMS)₂ = | sodium hexamethyldisilazide or sodium bis(trimethylsilyl)amide |
| Ph₃P = | triphenylphosphine |
| Pd(OAc)₂ = | Palladium acetate |
| (Ph₃P)₄Pd° = | tetrakis triphenylphosphine palladium |
| Pd₂(dba)₃ = | tris(dibenzylacetone)dipalladium |
| DPPF = | 1,1'-Bis(diphenylphosphino)ferrocene |
| HATU = | 2-(7-aza-1H-benzotriazole-1-yl)-1,1,3,3-tetramethyluronium hexafluorophosphate, 2-(3H-[1,2,3]triazolo[4,5-b]pyridin-3-yl)-1,1,3,3-tetramethylisouronium hexafluorophosphate(V) |
| DEAD = | diethyl azodicarboxylate |
| DIAD = | diisopropyl azodicarboxylate |
| Cbz—Cl = | benzyl chloroformate |
| CAN = | ceric ammonium nitrate |
| SAX = | Strong Anion Exchanger |
| SCX = | Strong Cation Exchanger |
| H₂ = | hydrogen |
| Ar = | argon |
| N₂ = | nitrogen |
| Equiv = | equivalent(s) |
| min = | minute(s) |
| h or hr = | hour(s) |
| L = | liter |
| mL = | milliliter |
| μL = | microliter |
| g = | gram(s) |
| mg = | milligram(s) |
| mol = | moles |
| mmol = | millimole(s) |
| meq = | milliequivalent |
| RT or R.T. = | room temperature |
| AT = | ambient temperature |
| sat or sat'd = | saturated |
| aq. = | aqueous |
| TLC = | thin layer chromatography |
| HPLC = | high performance liquid chromatography |
| HPLC R$_t$ = | HPLC retention time |
| LC/MS = | high performance liquid chromatography/mass spectrometry |
| MS or Mass Spec = | mass spectrometry |
| NMR = | nuclear magnetic resonance |
| NMR spectral data: | s = singlet; d = doublet; m = multiplet; br = broad; t = triplet |
| mp = | melting point |

EXAMPLES

The following working Examples serve to better illustrate, but not limit, some of the preferred embodiments of the present invention.

General

The term HPLC refers to a Shimadzu high performance liquid chromatography with one of following methods:

Method A: YMC or PHENOMENEX® C18 5 micron 4.6×50 mm column using a 4 minute gradient of 0-100% solvent B [90% MeOH: 10% H₂O:0.2% H₃PO₄] and 100-0% solvent A [10% MeOH:90% H₂O:0.2% H₃PO₄] with 4 mL/min flow rate and a 1 min. hold, an ultra violet (uv) detector set at 220 nm.

Method B: PHENOMENEX® S5 ODS 4.6×30 mm column, gradient elution 0-100% B/A over 2 min (solvent A=10% MeOH/H₂O containing 0.1% TFA, solvent B=90% MeOH/H₂O containing 0.1% TFA), flow rate 5 mL/min, UV detection at 220 nm.

Method C: YMC S7 ODS 3.0×50 mm column, gradient elution 0-100% B/A over 2 min (solvent A=10% MeOH/H₂O containing 0.1% TFA, solvent B=90% MeOH/H₂O containing 0.1% TFA), flow rate 5 mL/min, UV detection at 220 nm.

The term prep HPLC refers to an automated Shimadzu HPLC system using a mixture of solvent A (10% MeOH/90% H₂O/0.2% TFA) and solvent B (90% MeOH/10% H₂O/0.2% TFA). The preparative columns are packed with YMC or PHENOMENEX® ODS C18 5 micron resin or equivalent.

Synthesis of Intermediates

Intermediate 1

A.

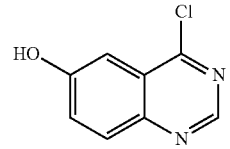

B.

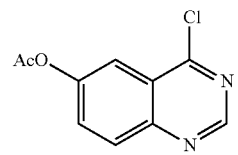 [SMILES: CC(=O)Oc1ccc2ncnc(Cl)c2c1]

*Bioorganic & Medicinal Chemistry Letters,* 14(1): 111-114 (2004).

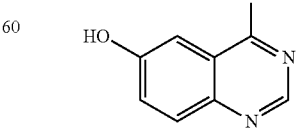

To a stirred solution of Part A compound (172 mg, 0.77 mmol) in methanol (3 mL) was added ammonia in methanol (7N, 6 mL, 42 mmol). After 1 h, the reaction was concentrated and water (20 mL) was added. The resulting mixture was filtered to collect Intermediate 1 (110 mg, 80%) as a white solid.

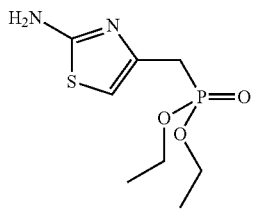

Intermediate 2

A.

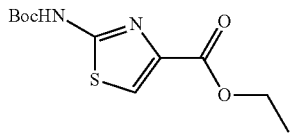 [SMILES: CCOC(=O)c1csc(NC(=O)OC(C)(C)C)n1]

A solution of di-tert-butyl dicarbonate (11.3 g; 51.83 mmol) in THF (50 mL) was added to a cold (0° C.) solution of ethyl 2-aminothiazole-4-carboxylate (8.59 g; 49.36 mmol) in THF (150 mL). TEA (7.57 mL; 54.30 mmol) was added followed by a catalytic amount of 4-DMAP (30 mg). The reaction mixture was stirred at RT for 16 h, then was concentrated in vacuo. The residue was partitioned between EtOAc (300 mL) and 0.5 N aqueous HCl (250 mL). The organic phase was washed with brine (150 mL), dried (MgSO$_4$) and concentrated in vacuo to give Part A compound (12.38 g; yield given below in Part B). The crude product was used in the next step without further purification.

B.

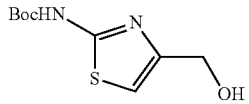

A solution of LiAlH$_4$ (1.0 M in THF) (48.0 mL; 48.0 mmol) was added to a cold (0° C.) solution of Part A compound (12.38 g; 45.3 mmol) in THF (130 mL). After 3 h at 0° C. the reaction was carefully quenched by dropwise addition of H$_2$O (5 mL). After 10 min, 5 N aqueous NaOH (2.5 mL) was added. After another 10 min, the solution was concentrated in vacuo. The residue was partitioned between EtOAc (300 mL) and H$_2$O (200 mL). The aqueous phase was extracted with EtOAc (100 mL). The combined organic phases were dried (MgSO$_4$) and concentrated in vacuo. The crude product was chromatographed (SiO$_2$; continuous gradient from 0 to 100% solvent B over 16 min, hold at 100% solvent B for 5 min, where solvent A=hexanes and solvent B=EtOAc) to give Part B compound (8.67 g; 67%—two steps).

C.

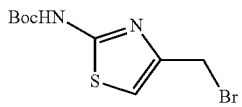

Method 1: A solution of methanesulfonyl chloride (318 μL; 4.10 mmol) in DCM (3 mL) was slowly added to a 0° C. solution of Part B compound (900 mg; 3.91 mmol) and TEA (600 μL; 4.30 mmol) in DCM (10 mL). After 25 min of stirring the reaction mixture was diluted with acetone (13 mL). LiBr (2.03 g; 23.46 mmol) was added. The reaction was stirred at RT for 1 h, then was diluted with sat. aqueous NH$_4$Cl (20 mL) and extracted with Et$_2$O (2×40 mL). The combined organic extracts were washed with sat. aqueous NH$_4$Cl (2×20 mL) and brine (20 mL). The solution was dried (MgSO$_4$) and concentrated in vacuo to give Part C compound (1.03 g; 89%). The crude product was taken forward without further purification.

Method 2: N-Boc thiourea (428 mg; 2.427 mmol) was added to a solution of 1,3-dibromoacetone (524 mg; 2.427 mmol) in acetone (9.7 mL). After 24 h at RT the reaction mixture was concentrated in vacuo to give Part C compound (0.78 g; Quant.) as a brown foam. The crude product was taken forward without further purification.

D.

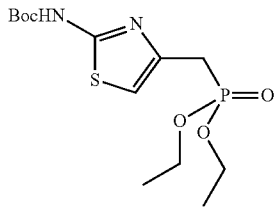 [SMILES: CCOP(=O)(Cc1csc(NC(=O)OC(C)(C)C)n1)OCC]

Triethyl phosphite (3.6 mL; 20.96 mmol) was added to a solution of Part C compound (878 mg; 2.99 mmol) in THF (6 mL). The reaction vessel was capped and the reaction mixture was heated at 80° C. for 16 h, then was cooled to RT. The solution was concentrated in vacuo. The crude product was chromatographed (SiO$_2$; continuous gradient from 0 to 100% solvent B over 8 min, hold at 100% solvent B for min, where solvent A=hexanes and solvent B=EtOAc) to give Part D compound (0.86 g; 82%).

E.

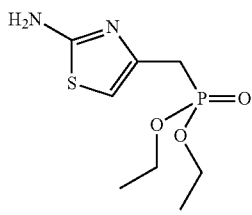

TFA (3.0 mL) was added to a 0° C. solution of Part D compound (0.86 g; 2.45 mmol) in DCM (7 mL). The reaction mixture was stirred at RT for 2.5 h, then was concentrated in vacuo. The residue was partitioned between EtOAc (15 mL) and sat. aqueous NaHCO$_3$ (10 mL). The aqueous phase was extracted with EtOAc (10 mL). The combined organic extracts were dried (MgSO$_4$) and concentrated in vacuo to give Intermediate 2 (488 mg; 80%). $^1$H NMR (400 MHz, CDCl$_3$) δ 6.17 (1H, d, J=3.95 Hz), 5.85 (2H, br. s.), 3.92-4.05 (4H, m), 3.08 (2H, d, J=21.09 Hz), 1.18 (6H, t, J=7.03 Hz).

Intermediate 3

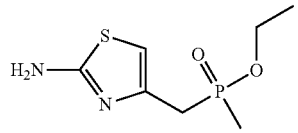

A.

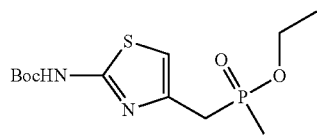 [SMILES: CCOP(C)(=O)Cc1csc(NC(=O)OC(C)(C)C)n1]

Diethyl methylphosphonite (690 mg; 5.07 mmol) was added to a solution of Intermediate 2, Part C compound (496 mg; 1.69 mmol) in THF (0.5 mL). The reaction mixture was heated at 75° C. for 16 h, then was cooled to RT. The solution was directly loaded onto a 12 g SiO$_2$ column and the crude product was chromatographed (continuous gradient from 0 to 100% EtOAc in hexanes over 4 min, switched to 5% MeOH in EtOAc and held for 10 min) to give Part A compound (493 mg; 91%) as a light yellow solid.

B.

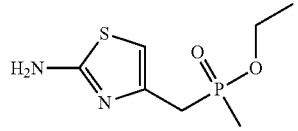

TFA (2.0 mL) was added to a 0° C. solution of Part A compound (768 mg; 2.40 mmol) in DCM (6 mL). The reaction mixture was stirred at RT for 3 h, then was concentrated in vacuo. The residue was partitioned between EtOAc (15 mL) and sat. aqueous NaHCO$_3$ (10 mL). The aqueous phase was extracted with EtOAc (2×10 mL). The combined organic extracts were dried (MgSO$_4$) and concentrated in vacuo to give Intermediate 3 (203 mg; 38%).

Intermediate 4

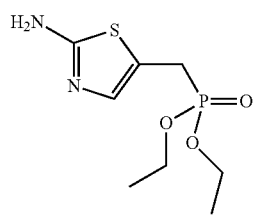

A.

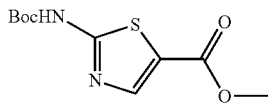 [SMILES: COC(=O)c1cnc(NC(=O)OC(C)(C)C)s1]

A solution of di-tert-butyl dicarbonate (1.66 g; 7.59 mmol) in THF (10 mL) was added to a 0° C. solution of methyl 2-aminothiazole-5-carboxylate (1.20 g; 7.59 mmol) in THF (20 mL). TEA (1.11 mL; 7.97 mmol) was added followed by a catalytic amount of 4-DMAP (10 mg). The reaction mixture was then stirred at RT for h, then was concentrated in vacuo. The residue was partitioned between EtOAc (80 mL) and 0.2 N aqueous HCl (40 mL). The organic phase was washed with brine (40 mL), dried (MgSO$_4$) and concentrated in vacuo to give Part A compound (1.70 g; yield given below in Part B). The crude product was taken forward without further purification.

B.

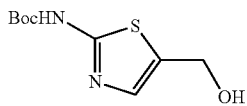

A solution of LiAlH$_4$ (7.60 mL of a 1.0 M solution in THF); 7.60 mmol) was added to a 0° C. solution of Part A compound (1.70 g; 6.58 mmol) in THF (30 mL). The reaction mixture was stirred at RT for 1 h, then was cooled to 0° C. and carefully quenched by dropwise addition of H$_2$O (0.76 mL). After 10 min, 5 N aqueous NaOH (0.38 mL) was added. After another 10 min, the solution was filtered through a pad of CELITE® and the filtrate was concentrated in vacuo. The crude product was chromatographed (SiO$_2$; continuous gradient from 0 to 100% solvent B over 13 min, hold at 100% solvent B for 6 min, where solvent A=hexanes and solvent B=EtOAc) to give Part B compound (0.80 g; 46%—two steps).

C.

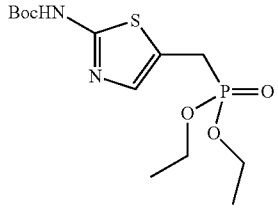

Part 1: Thionyl chloride (253 µL; 3.47 mmol) was added to a 0° C. mixture of Part B compound (200 mg; 0.869 mmol) in DCM (0.40 mL). The reaction mixture was stirred at 0° C. for 2 h then was concentrated vacuo to give the crude chloride.

Part 2: The crude chloride was dissolved in THF (3.0 mL). (EtO)$_3$P (1.20 mL; 6.95 mmol) was added. The reaction mixture was heated at 80° C. for 16 h, then was cooled to RT and concentrated in vacuo. The crude product was chromatographed (SiO$_2$; continuous gradient from 0 to 100% solvent B over 8 min, switch to solvent C, hold at 100% solvent C for 7 min, where solvent A=hexanes, solvent B=EtOAc and solvent C=3% MeOH in EtOAc) to give Part C compound (270 mg; 89%—two steps).

D.

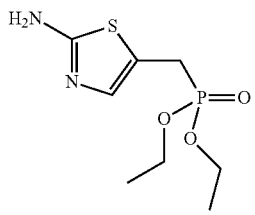

TFA (0.80 mL) was added to a 0° C. solution of Part C compound (0.31 g; 0.885 mmol) in DCM (2.4 mL). The reaction mixture was stirred at RT for 3 h then was concentrated in vacuo. The residue was partitioned between CHCl₃ (10 mL) and sat. aqueous NaHCO₃ (10 mL). The aqueous phase was extracted with CHCl₃ (10 mL). The combined organic extracts were dried (MgSO₄) and concentrated in vacuo to give Intermediate 4 (198 mg; 89%).

Intermediate 5

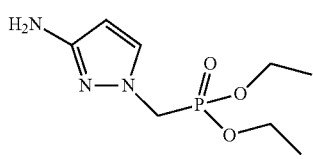

To a 0° C. solution of 1H-pyrazol-3-amine (1.00 g, 12.03 mmol) in DMF (25 mL) was added potassium tert-butoxide (2.70 g, 24.07 mmol) and the reaction mixture was stirred at 0° C. for 1 h. ICH₂PO₃Et₂ (3.35 g, 12.03 mmol) was added, and the reaction mixture was stirred at 0° C. for 1.5 h, then was allowed to warm to RT and stirred at RT overnight. Volatiles were removed in vacuo, and the residue was partitioned between brine (30 mL) and EtOAc (30 mL). The product was extracted with EtOAc (5×30 mL); the combined organic extracts were dried (MgSO₄), and concentrated in vacuo. The residue was purified by preparative HPLC (PHENOMENEX® Luna Axia 5 μm C18 30×100 mm column; detection at 220 nm; flow rate=40 mL/min.; continuous gradient from 100% A to 20% B over 25 min.+2 min. hold at 20% B, where A=90:10 H₂O:MeCN and B=90:10 MeCN:H₂O) to provide the Intermediate 5 (0.470 g, 16.8% yield) as a pale yellow oil. [M+H]⁺=233.9; ¹H NMR (400 MHz, CDCl₃): δ 7.29 (s, 1H), 5.66 (d, J=2.20 Hz, 1H), 4.36 (d, J=11.55 Hz, 2H), 4.10 (m, 4H), 3.76 (s, 2H) 1.29 (t, J=7.15 Hz, 6H).

Intermediate 6

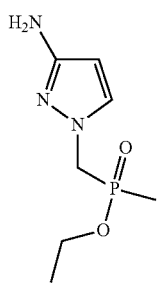

A.

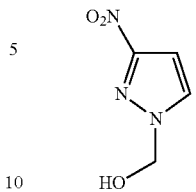

To a suspension of 3-nitro-1H-pyrazole (1.00 g, 8.84 mmol) in water (31 mL) was added formaldehyde (37 wt % in water, 1.317 mL, 17.69 mmol). The reaction mixture was stirred at RT for 48 h (after 2 h the reaction mixture became a homogeneous pale yellow solution). The reaction mixture was diluted with sat. aqueous NaHCO₃ (20 mL) and extracted with CH₂Cl₂ (4×40 mL) and EtOAc (3×50 mL). The combined organic extracts were dried (MgSO₄) and concentrated in vacuo to provide Part A compound (1.26 g, 99% yield) as a white solid. ¹H NMR (400 MHz, CD₃OD) δ 7.69 (d, J=2.20 Hz, 1H), 6.95 (d, J=2.75 Hz, 1H), 5.62 (d, J=7.70 Hz, 2H), 4.40 (t, J=7.70, 7.69 Hz, 1H).

B.

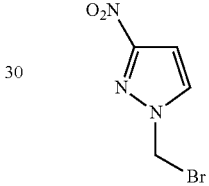

To a 75° C. solution of Part A compound (1.809 g, 12.64 mmol) in MeCN (54 mL) was added PBr₃ (1.788 mL, 18.96 mmol) dropwise over 10 min. The reaction mixture was stirred at 75° C. for 15 min, then was cooled to RT and filtered. The filter cake was washed with CH₃CN (2×2 mL), and the combined filtrates were concentrated in vacuo. The residue was partitioned between EtOAc (50 mL) and sat. aqueous NaHCO₃ (30 mL). The organic phase was washed with brine (20 mL), dried (MgSO₄), and concentrated in vacuo. The residue was chromatographed (SiO₂: continuous gradient 0% EtOAc/Hexane to 70% EtOAc/Hex) to provide Part B compound (1.693 g, 65% yield) as a pale yellow oil. ¹H NMR (400 MHz, CDCl₃) δ 7.80 (d, J=2.20 Hz, 1H), 7.01 (d, J=2.75 Hz, 1H), 5.98 (s, 2H).

C.

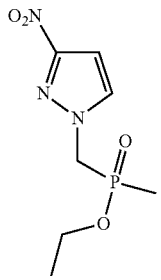

To a solution of Part B compound (1.7366 g, 8.43 mmol) in THF (4 mL) was added CH₃P(OEt)₂ (1.377 g, 10.12 mmol). The reaction mixture was stirred at 75° C. for 15 h. Additional CH$_3$P(OEt)$_2$ (0.53 g, 3.89 mmol) was added, and the reaction mixture was stirred at 75° C. for 24 h, then was cooled to RT. Volatiles were removed in vacuo, and the residue was chromatographed (SiO$_2$: continuous gradient from 0% MeOH/CH$_2$Cl$_2$ to 15% MeOH/CH$_2$Cl$_2$) to provide Part C compound (1.56 g, 80% yield) as an orange oil. [M+H]$^+$=234.1; $^1$H NMR (400 MHz, CDCl$_3$) δ 7.71 (d, J=3.30 Hz, 1H), 6.96 (d, J=2.75 Hz, 1H), 4.63 (d, J=9.34 Hz, 2H), 4.03-4.20 (m, 4H), 1.57 (d, J=14.85 Hz, 3H), 1.30-1.37 (m, 6H).

D.

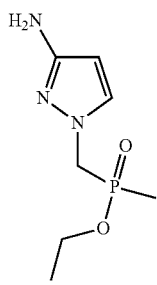

To a stirred solution of Part C compound (33 mg, 0.142 mmol) in MeOH (4 ml) was added palladium on carbon (15.06 mg, 0.014 mmol). The reaction put under Hydrogen gas, H$_2$ (0.285 mg, 0.142 mmol) for 3 h. HPLC showed reaction completed. The reaction was filtered through CELITE® and concentrated to give Intermediate 6 (25.6 mg, 89% yield) as a white solid.

The following Examples are illustrative of preferred compounds of the invention.

Example 1

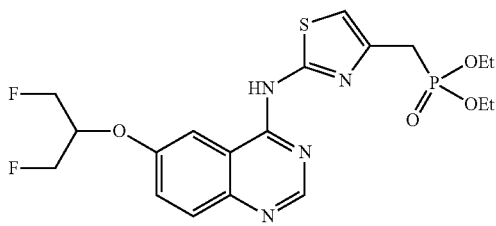 [SMILES: CCOP(=O)(Cc1csc(Nc2ncnc3ccc(OC(CF)CF)cc23)n1)OCC]

A.

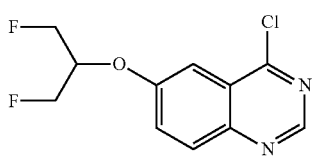 [SMILES: FCC(CF)Oc1ccc2ncnc(Cl)c2c1]

To a stirred solution of Intermediate 1 (70 mg, 0.39 mmol), 1,3-difluoro 2-propanol (112 mg, 1.16 mmol) and triphenyl phosphine (304 mg, 1.16 mmol) in THF (3 mL) was added DEAD (202 mg, 1.16 mmol) dropwise. The reaction was kept at RT for 2 h and was concentrated. The residue was diluted with CH$_2$Cl$_2$ and washed with sat NaHCO$_3$ solution. The organic phase was washed with brine (10 mL), dried (MgSO$_4$), and concentrated in vacuo. The resulting mixture was purified by silica gel column (10-100% EtOAc in hexanes) to give the Part A compound (80 mg, 80% yield) as a white solid.

B.

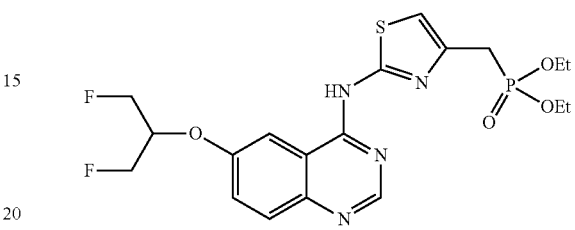

Method 1. Part A compound (0.02 g, 0.077 mmol), Intermediate 2 (0.023 g, 0.093 mmol), cesium carbonate (0.126 g, 0.387 mmol), palladium(II) acetate (0.347 mg, 1.546 mol) and BINAP (1.926 mg, 3.09 mol) were added to a microwave vessel and the solids were purged with Ar for 20 min. Toluene (1 mL) was added and the reaction vessel was evacuated and reequilibrated with Ar three times. The reaction mixture was then stirred at 80° C. for 2 h. The reaction mixture was filtered through CELITE®, the CELITE® cake was washed with EtOAc (2×5 mL) and the filtrate was concentrated in vacuo to a yellow/orange solid. The solid was purified by preparative HPLC (Sunfire 5u 19×100 mm column; detection at 220 nm; flow rate=20 mL/min; continuous gradient from 0% A to 100% B over 15 min+2 min hold time at 100% B, where A=90:10:0.1H$_2$O:MeOH:TFA and B=90:10:0.1 MeOH:H$_2$O:TFA) to give Example 1 (19 mg, 52%) as a yellow solid.

Method 2. A mixture of Part A compound (0.100 g, 0.387 mmol), Intermediate 2 (0.145 g, 0.580 mmol) and phenol (3.33 g, 35.4 mmol) in a 25 mL, 1 neck pear-shaped flask, that was equipped with a magnetic stirrer, an Ar inlet and a reflux condenser was heated to 140° C. in a hot oil bath for 12 h. The reaction mixture was partitioned between 1 N NaOH (40 mL) and EtOAc (15 mL), the phases were split, the aqueous phase was extracted with EtOAc (15 mL), the organic phases were combined, the composite was backwashed with 1 N NaOH (15 mL), dried over MgSO$_4$ and concentrated, in vacuo at 35° C., to a yellow oil. This was purified by preparative HPLC (Luna 5u 30×100 mm column; detection at 220 nm; flow rate=40 mL/min; continuous gradient from 20% A to 100% B over 25 min+2 min hold time at 100% B, where A=90:10 H$_2$O:MeOH and B=90:10 MeOH:H$_2$O) to give Example 1 (51 mg, 28%) as a yellow solid. [M+H]$^+$=473.4; $^1$H NMR (400 MHz, CD$_3$OD) δ ppm 1.30 (t, J=7.15 Hz, 6H), 3.42 (d, J=20.88 Hz, 2H), 4.05-4.17 (m, 4H), 4.66-4.79 (m, 2H), 4.78-4.86 (m, 2H), 4.99-5.18 (m, 1H), 6.98 (d, J=3.84 Hz, 1H), 7.58 (d, J=7.15 Hz, 1H), 7.78 (d, J=8.24 Hz, 1H), 8.02 (d, J=2.19 Hz, 1H), 8.61 (s, 1H).

Examples 2 to 7

Following the same procedures as described in Example 1, the following Examples 2 to 7 were prepared.

| Example No. | Structure | [M + H]⁺ | ¹H NMR (400 MHz, CDCl₃) δ, ppm | Yield and Description |
|---|---|---|---|---|
| 2 | (structure) | 437.0 | 1.30 (t, J = 7.15 Hz, 6 H), 1.43 (d, J = 6.05 Hz, 6 H), 3.41 (d, J = 20.89 Hz, 2 H), 4.02-4.23 (m, 4 H), 4.77-4.97 (m, 1 H), 6.99 (d, J = 4.40 Hz, 1 H), 7.47 (dd, J = 9.34, 2.74 Hz, 1 H), 7.71 (d, J = 9.34 Hz, 1 H), 7.86 (d, J = 2.75 Hz, 1 H), 8.51-8.67 (m, 1 H). | 37 mg (38%), yellow solid |
| 3 racemic | (structure) | 390.3 | 1.33 (t, J = 7.04 Hz, 3 H), 1.42 (d, J = 6.16 Hz, 6 H), 1.62 (d, J = 14.94 Hz, 3 H), 4.09-4.21 (m, 2 H), 4.72 (dd, J = 8.78, 3.07 Hz, 2 H), 4.82-4.89 (m, 1 H), 6.95 (d, J = 2.20 Hz, 1 H), 7.52 (dd, J = 8.79, 2.64 Hz, 1 H), 7.70 (dd, J = 2.19, 0.88 Hz, 1 H), 7.73 (d, J = 9.22 Hz, 1 H), 7.90 (d, J = 2.63 Hz, 1 H), 8.56 (s, 1 H). | 34 mg (61%), off-white solid |
| 4 | (structure) | 467.0 | 1.31 (t, J = 7.15 Hz, 6 H), 1.39 (d, J = 6.04 Hz, 3 H), 3.39-3.44 (d, J = 20.89 Hz, 2 H), 3.42 (s, 3 H), 3.57-3.70 (m, 3 H), 4.06-4.19 (m, 4 H), 7.03 (d, J = 3.85 Hz, 1 H), 7.53 (dd, J = 8.80, 2.75 Hz, 1 H), 7.73 (d, J = 8.79 Hz, 1 H), 7.93 (d, J = 2.75 Hz, 1 H), 8.60-8.69 (m, 1 H) | 27 mg (29%), yellow solid |
| 5 | (structure) | 450.4 | 1.31 (t, J = 7.15 Hz, 6 H), 1.38 (d, J = 6.05 Hz, 3 H), 3.41 (s, 3 H), 3.55-3.69 (m, 3 H), 4.07-4.21 (m, 4 H), 4.71 (d, J = 11.54 Hz, 2 H), 6.93 (s, 1 H), 7.49 (d, J = 7.69 Hz, 1 H), 7.65 (t, J = 2.20 Hz, 1 H), 7.71 (d, J = 8.80 Hz, 1 H), 7.83 (d, J = 2.20 Hz, 1 H), 8.47 (s, 1 H) | 90 mg (45.4%), white solid |
| 6 racemic | (structure) | 443.3 | 1.33 (t, J = 7.15 Hz, 3 H), 1.60 (d, J = 14.29 Hz, 3 H), 3.41 (d, J = 17.04 Hz, 2 H), 4.05-4.18 (m, 2 H), 4.67-4.78 (m, 2 H), 4.79-4.86 (m, 2 H), 4.99-5.19 (m, 1 H), 6.96 (d, J = 3.30 Hz, 1 H), 7.58 (d, J = 8.80 Hz, 1 H), 7.78 (d, J = 8.79 Hz, 1 H), 8.04 (d, J = 2.20 Hz, 1 H), 8.64 (s, 1 H) | 16.5 mg (7%), yellow solid |
| 7 | (structure) | 465.3 | 9.10 (s, 1H), 8.11 (m, 2H), 7.65 (dd, J = 8.6, 2.2 Hz, 1H), 7.14 (d, J = 4.0 Hz, 1H), 5.39 (m, 1H), 4.21 (m, 4H), 4.09 (m, 3H), 3.94 (m, 1H), 3.42 (d, J = 21.1 Hz, 2H), 2.45 (m, 1H), 2.17 (m, 1H), 1.36 (t, J = 7.0 Hz, 6H) | 5 mg (10.8%), white solid |

Assays for Glucokinase Activation

The compounds of formula I of the invention activate glucokinase. Assays which may be used in testing the compounds of formula I of the invention in activating glucokinase are known in the art such as disclosed in U.S. Pat. Nos. 6,320,050, 6,384,200 and 6,610,846 and WO 004/052869 and in Castellano, A. L. et al., "Glucokinase activating ureas", *Bioorg. Med. Chem. Letters*, 15:1501-1504 (2005), and Grimsby, J., et al., "Allosteric Activators of Glucokinase: Potential Role in Diabetes Therapy", *Science*, 301:370-373 (2003).

In general, compounds of the present invention, such as particular compounds disclosed in the following examples, have been identified to enhance the activity of glucokinase at concentrations equivalent to, or more potently than, 100 µM, preferably 10 µM, more preferably 1 µM, thereby demonstrating compounds of the present invention as especially effective enhancers of activity of glucokinase. Potencies can be calculated and expressed as either $EC_{50}$ (concentration to achieve 50% of full activation) and/or the maximum percentage activation above background, and refer to activity measured employing the assay system described above.

Assay and Biological Data

Compounds of formula I of the invention, including compounds described in the Examples hereof, have been tested in the following assay and have shown to be activators of glucokinase.

Glucokinase Tandem Enzymatic Assay

Enzymatic activity of human glucokinase (GK) was measured by incubating GK, ATP, and glucose for discrete time periods followed by quenching with EDTA (ethylenediamine tetra-acetic acid). Relative amounts of product glucose-6-phosphate (G6P) were measured by then running a detection assay using G6P dehydrogenase and measuring the conversion of ThioNAD (thio-nicotinamide adenine dinucleotide) to ThioNADH (thio-dihydronicotinamide adenine dinucleotide) at a wavelength of 405 nm. This "uncoupled" enzymatic reaction is denoted as the GK "tandem" assay. Activation of GK by compounds can be assessed using this assay. The GK tandem assay protocol described below was followed using a range of activator compound concentrations from 0 to 100 µM at 5 and 12 mM of glucose. Human full-length glucokinase (GK, 15 nM) was incubated with 5 or 12 mM glucose in a 384 well black microtiter plate with a clear bottom. To initiate the GK reaction, magnesium-ATP (3 mM final concentration) was added to GK in buffer (final buffer conditions of 25 mM HEPES buffer, pH 7.1, containing 1 mM dithiothreitol and 5% DMSO). The total reaction volume was 20 µL. The reaction was allowed to proceed for ten minutes and was then quenched with 5 µL EDTA; 45 mM final). The components of the detection reaction, ThioNAD and G6PDH (glucose-6-phosphate dehydrogenase) (final concentrations of 650 µM and 3.33 Units, respectively), were then added together in a volume of 25 µL, (to give a total volume of 50 µL). Absorbance measurements were made at 405 nm on a SPECTRAMAX® Plus 384 absorbance plate reader (Molecular Devices). Absorbance was read, background glucose-6-phosphate levels were subtracted, after which activation was calculated as a percentage of control activity. Control activity was determined using GK in the presence of vehicle (DMSO), with background glucose-6-phosphate subtracted. Background glucose-6-phosphate was determined by pre-quenching GK with EDTA prior to reaction initiation with ATP.

Expression and Purification of Human GK

Full-length human hepatic GK (untagged) was expressed in BL21 STAR (DE3)pLysS cells (Invitrogen) at 25° C. as described by Mookhtiar et al. (1). The protein was purified essentially as described by Lange (2) with a slight modification. Briefly, cell pellets were lysed via three rounds of freezing and thawing, centrifuged at 15000 g for clarification, and precipitated with 40-65% $(NH_4)_2SO_4$. The resulting pellet was resuspended in buffer, dialyzed, and applied directly to a Q-SEPHAROSE® (Sigma) column followed by elution with a linear 100-600 mM KCl gradient. GK containing fractions were pooled, dialyzed overnight vs. 25 mM Hepes pH 7.2/1 mM MgCl2/1 mM EDTA/0.1 M KCl/1 mM DTT, then dialyzed again with same buffer with 10% glycerol added.

REFERENCES

1. Mookhtiar, K. A. et al., "Heterologous expression and characterization of rat liver glucokinase regulatory protein", Diabetes, 45:1670-1677 (1996).
2. Lange, A. J. et al., "Expression and site-directed mutagenesis of hepatic glucokinase", Biochem. J., 277:159-163 (1991).

Biological data for select Examples are shown in the table below.

| Example No. | $EC_{50}$ (nM) with Human Glucokinase @ 12 mM Glucose |
|---|---|
| 1 | 91 |
| 2 | 136 |
| 6 | 390 |
| 3 | 810 |

For other Examples, the $EC_{50}$ values could not be calculated from the activation curves, so the maximal activation data (expressed as a % of basal activation) for some select Examples are shown in the table below.

| Example No. | Maximal activation (%) Human Glucokinase @ 12 mM Glucose |
|---|---|
| 3 | 134% |
| 1 | 145% |
| 4 | 180% |

In Vivo Studies: Oral Glucose Tolerance Test (OGTT)

Oral glucose tolerance tests were carried out on male DIO (diet-induced obese) C57BL/6J mice fed a high fat diet (60% kcal from fat) for 26 weeks prior to experimentation. Mice were fasted overnight before use for experiments. A test compound or vehicle (either: 1) 40% PEG 400+10% Cremophore+50% water or 2) 10% dimethyl acetamide+10% ethanol+10% Cremophore+70% water) was given orally 60 min before oral administration of a glucose solution at a dose of 2 g/kg body weight (oral glucose tolerance test; OGTT). Blood glucose levels were measured from tail-bled samples taken at different time points before and after administration of glucose (time course of 2 hours). A time curve of the blood glucose was generated and the change from baseline area-under-the curve (ΔAUC) from 0-120 min was calculated (the time glucose administration being time zero).

The examples in the table below reduced glucose AUC levels in an OGTT test in DIO mice as described above.

| Example No. | Reduction in Glucose AUC at 30 µmol/kg dose |
|---|---|
| 1 | 93% |

What is claimed is:

1. A compound having the structure

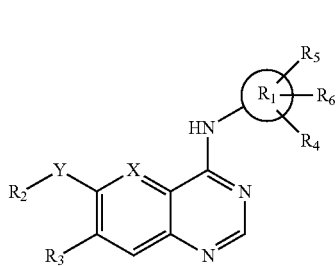

wherein
- $R_1$ is a 5- or 6-membered monocyclic heteroaryl substituted by $R_4$, and optionally substituted with one or two substituents $R_5$ and/or $R_6$, wherein the heteroaryl possesses a nitrogen atom adjacent to —NH—;
- $R_4$ is —$(CH_2)_n$—Z—$(CH_2)_m$—$PO(OR_7)(OR_8)$,
- or —$(CH_2)_n$Z—$(CH_2)_m$—$PO(OR_7)R_9$,
- or —$(CH_2)_n$—Z—$(CH_2)_m$—O—$PO(OR_7)R_9$,
- or —$(CH_2)_n$Z—$(CH_2)_m$—O—PO—$(R_9)R_{10}$,
- or —$(CH_2)_n$Z—$(CH_2)_m$—$PO(R_9)R_{10}$,
- where $R_4$ is connected to $R_1$ through a ring nitrogen or carbon;
- $R_7$ and $R_8$ are the same or different and are independently selected from $C_1$-$C_3$ alkyl;
- $R_9$ and $R_{10}$ are the same or different and are independently selected from $C_1$-$C_3$ alkyl, phenyl, phenyl-$C_1$-$C_3$-alkyl, 5- to 6-membered heteroaryl and 5- to 6-membered heteroaryl-$C_1$-$C_3$-alkyl, any of which may be optionally substituted;
- additionally, $R_7$ and $R_8$ can be cyclized into a ring

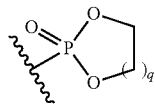

where q=1 to 3;
similarly, $R_7$ and $R_9$ can be cyclized into a ring

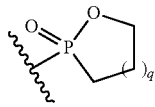

where q=1 to 3, or

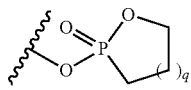

where q=1 to 3;
similarly, $R_9$ and $R_{10}$ can be cyclized into a ring

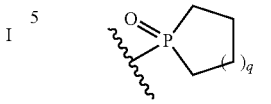

where q=1 to 3, or

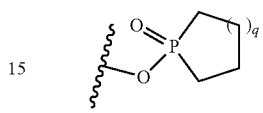

where q=1 to 3;
- Z is selected from a bond, $C_1$-$C_3$ alkylene and $C_2$-$C_4$ alkenylene, each of which may be optionally substituted with hydroxy, $C_1$-$C_3$ alkoxy, amino-$C_1$-$C_3$-alkyl, aminophenyl-$C_1$-$C_3$-alkyl, 5- to 6-membered heteroaryl-$C_1$-$C_3$-alkyl, amino 5- to 6-membered heteroaryl-$C_1$-$C_3$-alkyl, 5- to 6-membered heteroaryl-$C_1$-$C_3$-alkyl, aminophenyl, amino 5- to 6-membered heteroaryl, or carboxy;
- m is 0, 1 or 2;
- n is 0, 1 or 2;
- and Z may be O, S, $SO_2$ when
- m is 1 or 2 or
- n is 1 or 2;
- $R_5$ and $R_6$ are the same or different and are independently selected from hydrogen, $C_1$-$C_3$ alkyl, halogen or carboxyl, or is absent;
- X is N or CH;
- Y is O or S;
- $R_3$ is H, halogen, $C_1$-$C_3$ alkyl, OH, $OCH_3$, SH, or $SCH_3$;
- $R_2$ is $C_1$-$C_6$ alkyl, branched $C_3$-$C_6$ alkyl, $C_3$-$C_6$ cycloalkyl, $C_3$-$C_6$ cycloalkylalkyl, phenyl, phenyl-$C_1$-$C_3$-alkyl, 5- to 6-membered heteroaryl, 4- to 7-membered heterocyclyl, or 5- to 6-membered heteroaryl-$C_1$-$C_3$-alkyl;
- wherein each $R_2$ is independently substituted by zero to three $R_{11}$ groups;
- each $R_{11}$ is independently selected from halogen, —$CH_{(3-a)}F_a$, CN, $NO_2$, $NH_2$, $C_1$-$C_3$ alkyl, O-$C_1$-$C_3$-alkyl, —COOH, OH, phenyloxy, 5- to 6-membered heteroaryloxy, 4- to 7-membered heterocyclyloxy, —S—$R_{12}$, —S(O)—$R_{12}$, —$SO_2R_{13}$, —$SO_2NR_{14}R_{15}$, —$NR_{14}R_{15}$, —$CO_2R_{13}$, —$C(O)NR_{14}R_{15}$, —$NR_7C(O)R_{15}$, —$NR_7SO_2R_{12}$, —$NR_7CO_2R_{12}$, —$OCONR_{14}R_{15}$, —$NR_7C(O)NR_{14}R_{15}$, phenyl, 5- to 6-membered heteroaryl, or 4- to 7-membered heterocyclyl;
- wherein each phenyl, heteroaryl, or heterocyclyl ring in $R_{11}$ is optionally substituted by halogen, —$CH_{(3-a)}F_a$, CN, $NO_2$, $NH_2$, —COOH, OH, $C_1$-$C_3$ alkyl, —O—$C_1$-$C_3$-alkyl, —C(O)O-$C_1$-$C_3$-alkyl, —$NR_{14}R_{15}$, —C(O)$NR_{14}R_{15}$, —$NR_7COR_{15}$, —$NR_7SO_2R_{12}$, —$NR_7COOR_{12}$, —$NR_7CONR_{14}R_{15}$, or —$SO_2NR_{14}R_{15}$;
- each "a" is independently an integer selected from 1, 2 or 3;
- each $R_{12}$ is independently selected from $C_1$-$C_3$ alkyl, phenyl, 5- to 6-membered heteroaryl, phenyl-$C_1$-$C_3$-alkyl, and/or 5- to 6-membered heteroaryl-$C_1$-$C_3$-alkyl;
- each $R_{13}$ is independently selected from H, $C_1$-$C_3$ alkyl, phenyl, 5- to 6-membered heteroaryl, phenyl-$C_1$-$C_3$-alkyl, and/or 5- to 6-membered heteroaryl-$C_1$-$C_3$-alkyl;

R$_{14}$ and R$_{15}$ are the same or different and are independently selected from H, C$_1$-C$_3$ alkyl, C$_3$-C$_6$ cycloalkyl, phenyl, phenyl-C$_1$-C$_3$-alkyl, 5- to 6-membered heteroaryl, and/or 5- to 6-membered heteroaryl-C$_1$-C$_3$-alkyl; or R$_{14}$ and R$_{15}$ cyclized together to form a 3- to 7-membered heterocyclyl; and all stereoisomers thereof, a prodrug ester thereof, or a pharmaceutically acceptable salt thereof.

2. The compound as defined in claim 1 where X is CH.

3. The compound as defined in claim 1 wherein the moiety

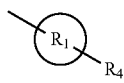

is:

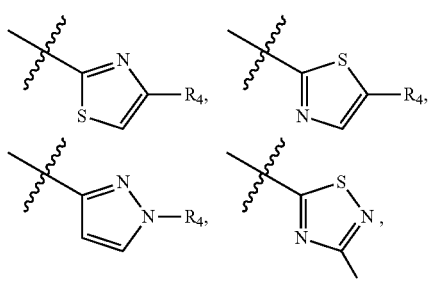

4. The compound as defined in claim 1 wherein R$_4$ is —(CH$_2$)$_n$—Z—(CH$_2$)$_m$—PO(OR$_7$)(OR$_8$) or —(CH$_2$)$_m$—Z—(CH$_2$)$_m$—PO(OR$_7$)R$_9$ where Z is a bond and n is 1 or 2.

5. The compound as defined in claim 1 wherein R$_4$ is:

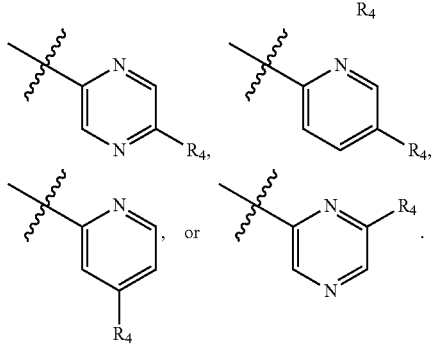

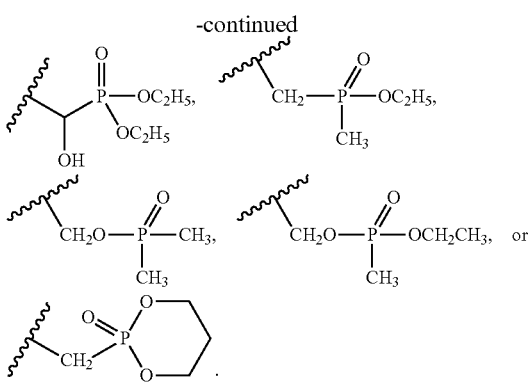

6. The compound as defined in claim 1 wherein R$_5$ and R$_6$ are each H, and Z is a bond or CH.

7. The compound as defined in claim 1 wherein
R$_3$ is H;
R$_4$ is

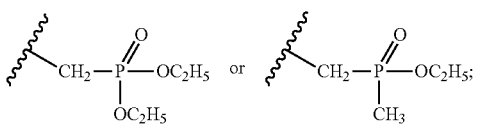

Y is O; and
R$_2$ is C$_1$-C$_3$ alkyl substituted with zero to two R$_{11}$, or 4- to 7-membered heterocyclo; and
each R$_{11}$ is independently selected from halogen and/or —O—C$_1$-C$_3$-alkyl.

8. The compound as defined in claim 7 wherein:
R$_2$ is

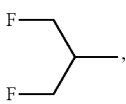

i-propyl,

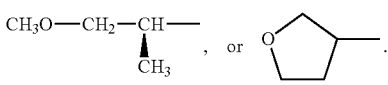

9. The compound as defined in claim 1 wherein R$_4$ is —(CH$_2$)$_n$—Z—(CH$_2$)$_m$—PO—(OR$_7$)(OR$_8$) wherein Z is a bond and n is 1 or 2.

10. The compound as defined in claim 1 having the structure

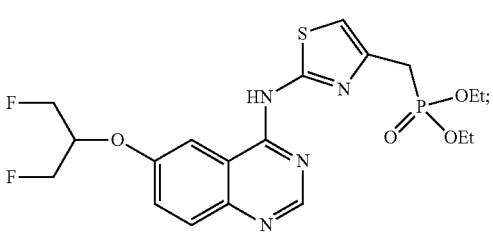

-continued

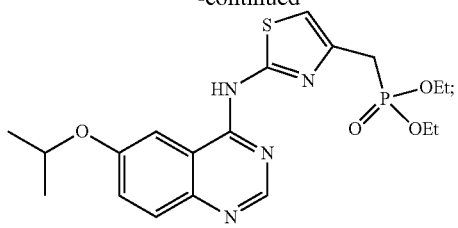

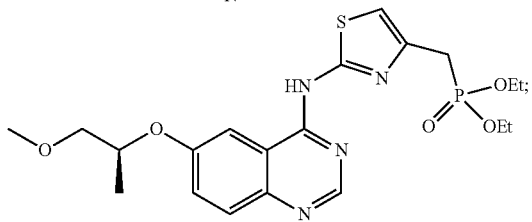

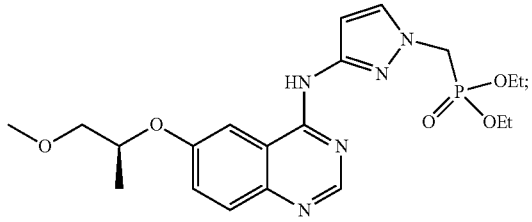

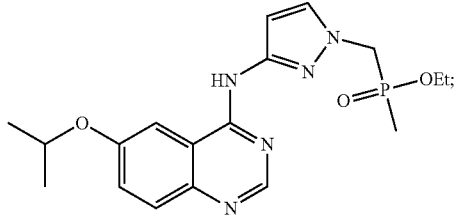

-continued

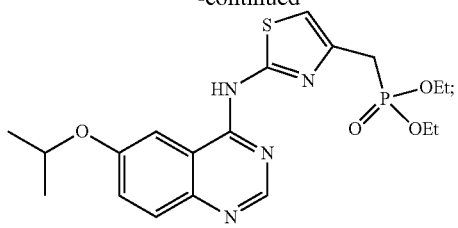  ; or

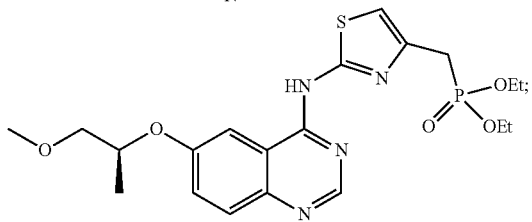

or a pharmaceutically acceptable salt thereof.

11. A pharmaceutical composition comprising a compound as defined in claim 1 and a pharmaceutically acceptable carrier thereof.

12. A compound according to claim 1 or a pharmaceutically acceptable salt thereof, for use in therapy in treating diabetes, hyperglycemia, impaired glucose tolerance, insulin resistance, hyperinsulinemia, retinopathy, neuropathy, nephropathy, atherosclerosis, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, lipid disorders.

* * * * *

UNITED STATES PATENT AND TRADEMARK OFFICE
CERTIFICATE OF CORRECTION

PATENT NO.       : 8,592,396 B2                                    Page 1 of 1
APPLICATION NO.  : 13/640767
DATED            : November 26, 2013
INVENTOR(S)      : Wei Meng et al.

It is certified that error appears in the above-identified patent and that said Letters Patent is hereby corrected as shown below:

In the Claims:

Claim 4:

Column 67, line 48, change "—(CH$_2$)$_m$—" to -- —(CH$_2$)$_n$— --. (second occurrence)

Signed and Sealed this
Tenth Day of June, 2014

Michelle K. Lee
*Deputy Director of the United States Patent and Trademark Office*